US011419317B2

(12) United States Patent
Poluektova et al.

(10) Patent No.: US 11,419,317 B2
(45) Date of Patent: Aug. 23, 2022

(54) NON-HUMAN ANIMAL HAVING HUMAN IL-34 AND USE THEREOF

(71) Applicants: Central Institute for Experimental Animals, Kawasaki (JP); the Board of Regents of the University of Nebraska, Lincoln, NE (US)

(72) Inventors: Larisa Poluektova, Omaha, NE (US); Santhi Gorantla, Omaha, NE (US); Mamoru Ito, Kawasaki (JP); Ikumi Katano, Kawasaki (JP)

(73) Assignees: Central Institute for Experimental Animals, Kawasaki (JP); the Board of Regents of the University of Nebraska

( * ) Notice: Subject to any disclaimer, the term of this patent is extended or adjusted under 35 U.S.C. 154(b) by 0 days.

(21) Appl. No.: 16/615,578

(22) PCT Filed: Mar. 18, 2019

(86) PCT No.: PCT/JP2019/011261
§ 371 (c)(1),
(2) Date: Nov. 21, 2019

(87) PCT Pub. No.: WO2020/157997
PCT Pub. Date: Aug. 6, 2020

(65) Prior Publication Data
US 2021/0352877 A1    Nov. 18, 2021

Related U.S. Application Data

(60) Provisional application No. 62/797,369, filed on Jan. 28, 2019.

(51) Int. Cl.
*A01K 67/027* (2006.01)
*C12N 5/079* (2010.01)

(52) U.S. Cl.
CPC ........ *A01K 67/027* (2013.01); *A01K 67/0271* (2013.01); *A01K 67/0275* (2013.01); *C12N 5/0622* (2013.01); *A01K 2207/12* (2013.01); *A01K 2207/15* (2013.01); *A01K 2227/105* (2013.01); *A01K 2267/0337* (2013.01)

(58) Field of Classification Search
CPC .............. A01K 67/027; A01K 67/0271; A01K 67/0275; A01K 2207/12; A01K 2207/15; A01K 2227/105; A01K 2267/0337; C12N 5/0622
USPC .......................................................... 800/9
See application file for complete search history.

(56) References Cited

FOREIGN PATENT DOCUMENTS

| CN | 101179931 A | 5/2008 |
| CN | 102725400 A | 10/2012 |
| CN | 107660152 A | 2/2018 |
| WO | 2018/200669 A1 | 11/2018 |

OTHER PUBLICATIONS

Chen (2016, JCI Insight, 1(19):e88632, 12 pages).*
Greter (2012, Immunity, 37, pp. 1050-10660).*
Cheng (2017, PlosOne, 12(6):e0179605, 16 pages).*
Capotondo, A., et al. Brain conditioning is instrumental for successful microglia reconstitution following hematopoietic stem cell transplantation. Proc Natl Acad Sci USA 109, 15018-15023 (2012).
Asheuer, M., et al. Human CD34+ cells differentiate into microglia and express recombinant therapeutic protein. Proc Natl Acad Sci USA 101, 3557-3562 (2004).
Araínga, M., Su, H., Poluektova, L.Y., Gorantla, S. & Gendelman, H.E. HIV-1 cellular and tissue replication patterns in infected humanized mice. Sci Rep 6, 23513 (2016).
Gorantla, S., et al. Links between progressive HIV-1 infection of humanized mice and viral neuropathogenesis. Am J Pathol 177, 2938-2949 (2010).
Denton, P.W. & Garcia, J.V. Novel humanized mouse models for HIV research. Curr HIV/AIDS Rep 6, 13-19 (2009).
Dash, P.K., et al. Loss of neuronal integrity during progressive HIV-1 infection of humanized mice. The Journal of neuroscience: the official journal of the Society for Neuroscience 31, 3148-3157 (2011).
Qing Yang et al., The Establishment of Interleukin 34 Transgenic mice, Chinese Journal of Comparative Medicine, Jun. 2011, vol. 21, No. 6, pp. 64-66, 59.
Suwen Wei et al, Functional overlap but differential expression of CSF-1 and IL-34 in their CSF-1 receptor-mediated regulation of myeloid cells, Journal of Leukocyte Biology, May, 26, 2010, vol. 88, No. 3, pp. 495-505.
Suzumura Akio, Microglia in neuroimmunological disorders, Nippon Rinsho (Separate volume), Immunological neurological disease, vol. 73, Suppl. 7, 2015, pp. 66-72.
Dominic Paquin-Proulx et al, Human interleukin-34-derived macrophages have increased resistance to HIV-1 infection, Cytokine, Sep. 19, 2018, vol. 111, pp. 272-277.
Saumi Mathews et al., The HIV reservoir in a humanized mouse brain. Abstracts from the Joint Meeting of the International Society for NeuroVirology (ISNV) and the Society on NeuroImmune Pharmacology (SNIP) Apr. 10-14, 2018, Chicago, Illinois, USA, p. 185.
International Search Report issued in international application No. PCT/JP2019/011261 dated May 14, 2019.

(Continued)

*Primary Examiner* — Valarie E Bertoglio
(74) *Attorney, Agent, or Firm* — Fox Rothschild LLP

(57) ABSTRACT

The present invention provides a non-human animal having human interleukin-34 (IL-34) in the body thereof; a method for producing a non-human animal having human microglia, which includes transplanting human CD34-positive hematopoietic stem cells into the non-human animal having human IL-34 in the body; and a method for producing human microglia, which includes obtaining human microglia from the non-human animal having human microglia.

6 Claims, 17 Drawing Sheets
Specification includes a Sequence Listing.

(56) References Cited

OTHER PUBLICATIONS

Geng Yue et al., "Polarization of microglia and factors influencing them in ischemic brain injury", <Chinese Journal of Neuroanatomy Chinese Journal of Neuroanatomy>, No. 4, pp. 139 to 143.

Chen-Jiang Hao, "Research Progress on Central Nervous System HIV-1 Infection", <Shandong Medical Journal>, No. 10, pp. 108 to 111.

Llewellyn George N et al. "HIV-1 infection of microglial cells in a reconstituted humanized mouse model and identification of compounds that selectively reverse HIV latency", Journal of Neurovirology, Informa Healthcare, GB, vol. 24, No. 2, Dec. 18, 2017 (Dec. 18, 2017), pp. 192-203.

Tim Willinger et al. "Improving human hemato-lymphoid-system mice by cytokine knock-in gene replacement", Trends in Immunology, vol. 32, No. 7, Jul. 2011 (Jul. 2011), pp. 321-327.

Mathews Saumi et al. "HIV-1 induced neuropahhology of a humanized microglial mouse", Mar. 1, 2019 (Mar. 1, 2019), XP055897358, Retrieved from the Internet: URL: https://2jg4quetidw2blbbq2ixwziw-wpengine.netdna-ssl.com/wp-content/uploads/sites/2/posters/2019/1430_Mathews_0433.pdf, 1 page.

Qing Yang et al., "The Establishment of Interleukin 34 Transgenic mice", Chinese Journal of Comparative Medicine, Jun. 2011, vol. 21, No. 6, pp. 64-66, 59, 90, XP055821401.

Office Action dated Mar. 2, 2022 in Chinese Application No. 201980090496.7, 29 pages.

Supplementary European Search Report dated Mar. 16, 2022 in European Application No. 19914084.9, 5 pages.

Office Action dated Mar. 28, 2022 in European Patent Application No. 19914084.9, 5 pages.

\* cited by examiner

■ 261 Up regulated
□ 426 Down regulated

NON-HUMAN ANIMAL HAVING HUMAN IL-34 AND USE THEREOF

Priority is claimed on U.S. Patent Application No. 62/797,369, filed Jan. 28, 2019, the content of which is incorporated herein by reference.

STATEMENT AS TO FEDERALLY SPONSORED RESEARCH

This invention was made with government support under Grant #R21 DA041018 awarded by the National Institutes of Health. The government has certain rights in the invention.

TECHNICAL FIELD

The present invention relates to a non-human animal having human IL-34 and the use thereof. The present invention particularly relates to a non-human animal having human IL-34, a method for producing human microglia using the non-human animal, and human microglia obtained from the non-human animal. In addition, the present invention relates to a method for producing a non-human animal having human microglia, and a method for producing an HIV-infected non-human animal.

BACKGROUND ART

Microglia are central nervous system (CNS)-resident macrophages, and contribute to brain development and immune defense. However, the precise origin, development, and specific markers of human microglia have been subjects of debate. In the adult brain, it is unclear whether microglia are derived only from cells present in the brain from a fetal developmental stage, or whether microglia flow into the CNS from hematopoietic stem cells (HSCs) or monocytes, under both normal or pathological conditions. Monocytes enter the parenchyma of the CNS and can be changed to cells that are morphologically similar to microglia. However, such changes occur only under certain conditions, and it has been discussed whether these cells are genuinely microglia. In mouse-to-mouse transplantation experiments, HSCs derived from a donor were shown to produce microglia-like cells in mice depleted of endogenous microglia by the expression of microglia-specific suicide genes, radiation, or chemical substances (for example, Non-Patent Literature 1).

On the other hand, attempts to efficiently generate human microglia in the brains of immunodeficient mice have not been successful. In an experiment in which human CD34[+] cells were transplanted into immunodeficient mice, only a few human microglia were confirmed (for example, Non-Patent Literature 2).

Existing humanized mice are mice in which human immune cells have been stably reconstructed by transfer of HSC (for example, Non-Patent Literature 3 and Non-Patent Literature 4) or human fetal liver and thymus (for example, Non-Patent Literature 5) into NOD/ScidIL2Rg-/-(NSG) mice and the like. However, in the mouse brain, the number and distribution of macrophages in the vicinity of meninges and blood vessels are low, and hardly any microglia have been recognized (Non-Patent Literature 4 and Non-Patent Literature 6). Since microglial cells are the main target of HIV-1 and the main reservoir of HIV-1 in the CNS, humanized mouse models currently usable for analysis of intracerebral microglial cells are insufficient for simulating HIV-1 infection in the CNS in humans.

CITATION LIST

Non-Patent Literature

[Non-Patent Literature 1]
Capotondo, A., et al. Brain conditioning is instrumental for successful microglia reconstitution following hematopoietic stem cell transplantation. Proc Natl Acad Sci USA 109, 15018-15023 (2012).

[Non-Patent Literature 2]
Asheuer, M., et al. Human CD34+ cells differentiate into microglia and express recombinant therapeutic protein. Proc Natl Acad Sci USA 101, 3557-3562 (2004).

[Non-Patent Literature 3]
Arainga, M., Su, H., Poluektova, L. Y., Gorantla, S. & Gendelman, H. E. HIV-1 cellular and tissue replication patterns in infected humanized mice. Sci Rep 6, 23513 (2016).

[Non-Patent Literature 4]
Gorantla, S., et al Links between progressive HIV-1 infection of humanized mice and viral neuropathogenesis. Am J Pathol 177, 2938-2949 (2010).

[Non-Patent Literature 5]
Denton, P. W. & Garcia, J. V. Novel humanized murine models for HIV research. Curr HIV/AIDS Rep 6, 13-19 (2009).

[Non-Patent Literature 6]
Dash, P. K., et al. Loss of neuronal integrity during progressive HIV-1 infection of humanized mice. The Journal of neuroscience: the official journal of the Society for Neuroscience 31, 3148-3157 (2011).

SUMMARY OF INVENTION

Technical Problem

As described above, humanized mice of the related art cannot retain human microglia, or can retain only a small number thereof, and thus have not been suitable for simulating HIV infection and the like in humans.

An object of the present invention is to provide a non-human animal that retain a large number of human microglia, and a method for producing the same. Another object of the present invention is to provide a method for using the non-human animal.

Solution to Problem

The present invention includes the following aspects.

[1] A non-human animal having human interleukin-34 (IL-34) in the body thereof.

[2] The non-human animal according to [1], to which a human CD34-positive hematopoietic stem cell is transplanted.

[3] The non-human animal according to [1] or [2], in which human microglia are present in the brain.

[4] The non-human animal according to [3], in which the human microglia express at least one gene selected from the group consisting of CD74, b2m, AIF1, CD14, CD68, CSF1R, ITGAM (CD11b), P2RY12, CX3CR1, TREM2, TMEM119, CCL2, TNF, HGH (IL-6), CXCL8, IL-10, IL-1a, CXCL10, PU.1 (SPI1), ETV5, and APOE.

[5] The non-human animal according to [3] or [4], in which the human microglia secrete at least one cytokine selected from the group consisting of CCL2, TNF, HGH (IL-6), CXCL8, IL-10, IL-1a, and CXCL10.

[6] The non-human animal according to any one of [1] to [5], which is infected with the human immunodeficiency virus (HIV).

[7] A method for producing human microglia, including obtaining human microglia from the non-human animal according to any one of [3] to [6].

[8] A method for producing a non-human animal having human microglia, including transplanting human CD34-positive hematopoietic stem cells into a non-human animal having human IL-34 in the body thereof.

[9] The method for producing a non-human animal having human microglia according to [8], in which the non-human animal having human IL-34 in the body is an immunodeficient non-human animal.

[10] The method for producing a non-human animal having human microglia according to [8] or [9], in which the human microglia are present in the brain.

[11] The method for producing a non-human animal having human microglia according to any one of [8] to [10], in which the human microglia express at least one gene selected from the group consisting of CD74, b2m, AIF1, CD14, CD68, CSF1R, ITGAM (CD11 b), P2RY12, CX3CR1, TREM2, TMEM119, CCL2, TNF, HGH (IL-6), CXCL8, IL-10, IL-1a, CXCL10, PU.1 (SPI1), ETV5, and APOE.

[12] The method for producing a non-human animal having human microglia according to any one of [8] to [11], in which the human microglia secrete at least one cytokine selected from the group consisting of CCL2, TNF, HGH (IL-6), CXCL8, IL-10, IL-1a, and CXCL10.

[13] A method for producing an HIV-infected non-human animal, including producing a non-human animal having human microglia by the method for producing a non-human animal having human microglia according to any one of [8] to [12], and then infecting the non-human animal having human microglia with HIV.

The present invention also includes the following aspects.

[14] The non-human animal according to any one of [1] to [6], which secretes human IL-34.

[15] The non-human animal according to [14], which has a human IL-34 gene.

[16] The non-human animal according to [14] or [15], which has human microglia.

[17] The non-human animal according to any one of [1] to [6] and [14] to [16], which is a rodent.

[18] The non-human animal according to [17], which is a mouse.

[19] A method for producing the non-human animal having human microglia according to any one of [7] to [12], in which the non-human animal having human IL-34 in the body has a human IL-34 gene.

[20] A method for producing the non-human animal having human microglia according to any one of [7] to [12] and [19], in which the non-human animal having human IL-34 in the body secretes human IL-34.

[21] A method for producing the non-human animal having human microglia according to any one of [7] to [12], [19], and [20], in which the non-human animal is a rodent.

[22] A method for producing the non-human animal having human microglia according to [21], in which the rodent is a mouse.

Advantageous Effects of Invention

According to the present invention, a non-human animal having large retention numbers of human microglia and a method for producing the same are provided. A method for using the non-human animal is also provided.

BRIEF DESCRIPTION OF DRAWINGS

FIG. 1A shows a vector introduced into NOG-hIL-34 transgenic mice for producing NOD. Cg-Prkdc$^{scid}$Il2rg$^{tm1Sug}$ (CMV-IL-34) 1/Jic mice. A vector containing hIL-34 and a transgene (Tg) is inserted downstream of a CMV promoter.

FIG. 1B shows results of PCR analysis using DNA extracted from the ears of homozygous mice. In NOG-hIL-34 transgenic mice (IL-34+/+), a band was not detected in control non-transgenic NOG mice in which the band of hIL-34 (358 bp) was amplified.

FIG. 1C shows the results of real-time PCR using RNA extracted from the brain, spleen, lung, kidney, liver, and skin of NOG-hIL-34 mice. In NOG-hIL-34 (IL-34), the expression of hIL-34 in all tissues was confirmed in contrast to in NOG mice (Control).

FIG. 1D shows the results of ELISA that confirmed hIL-34 expression in plasma.

FIG. 3A shows the results of FACS analysis of peripheral blood. By gating to the CD45 lymphocyte population, representative plots of differentiated 45 (CD45)+, and human clusters of human CD3, CD19, and CD14 cells can be confirm.

FIG. 3B shows a percentage of human cell subpopulations in the peripheral blood of reconstituted mice. Each symbol represents an individual mouse.

FIG. 4A is a diagram comparing tissue macrophage reconstitution between CD34-NOG-hIL-34 and CD34-NSG mice. Brain sections were stained for HLA-DR, and liver and spleen were stained for CD68.

FIG. 4B shows human cells stained with human P2RY127, CD14, CD68, and CD163 antibodies in the brain.

FIG. 4C shows an enlarged view of the olfactory bulb (OB, 20×), cortex (CTX, 20×), and hippocampus (HC, 10×) from the brains of CD34-NOG-hIL-34 mice in which HLA-DR was stained.

FIG. 4D is a diagram showing microglia morphology at higher magnification.

FIG. 4E is a confocal image of the brain for which HLA-DR and Iba-1 were stained.

FIG. 4F shows a percentage of HLA-DR/Iba-1 double-positive human microglial cells in all Iba-1$^+$ cells. Brain stem (BS), Midbrain (MB), Cerebellum (CB), Cerebral cortex (CC), Hippocampus (HC), and Olfactory bulb (OB).

FIG. 5A shows a representative CD34-NOG-hIL-34 mouse brain at 2× magnification. An overall image of human microglial distribution in the entire mouse brain area can be confirmed. Olfactory bulb (OB), Cerebral cortex (CTX), Hippocampus (HC), Midbrain (MB), Cerebellum (CB), Striatum (STR), Hippocampus (HC), Substantia nigra (SN), Thalamus (TH), and Brain stem (BS). The image was taken with a Ventana iScan HT at 200× original magnification. A magnified view (20× objective lens) of the brain region (OB, CTX, and HC in FIG. 4C) shows HLA-DR$^+$ cells having the morphology of microglia.

FIG. 5B shows a representative CD34-NSG mouse brain section (2×) showing the absence of human microglial cells. A small number of HLA-DR$^+$ cells found in the meninges and perivascular area (boxed area) are shown in an enlarged view (20×).

FIG. 8A shows a viral load of peripheral blood obtained by a COBAS Amplicor System. Each symbol represents an individual infected mouse.

FIG. 8B shows the results of flow cytometric analysis of splenocytes for human CD4- and CD8-positive T lymphocytes. A percentage of CD4- and CD8-positive cells is shown.

FIG. 8C shows the results of flow cytometric analysis of splenocytes for human CD4 and CD8-positive T lymphocytes. A CD4/CD8 ratio in an HIV$^+$ group (n=12) and control group (n=7) in spleen is shown.

FIG. 8D shows the results of immunohistological analysis of spleen sections showing the presence of HLA-DR$^+$ cells and HIV-1-infected cells stained for HIV-1 p24. RNAScope assay was performed using V-HIV1-Clade-B (ACD cat #416111), an antisense probe targeting HIV-1 at 854 to 8291 bp, and HIV-1 RNA was detected as a single brown dot or cluster of dots in spleen sections with a thickness of 5 μm. In uninfected mice, no signal corresponding to the presence of viral RNA was detected. Images were taken with a Nuance multiplex system at 200× original magnification.

FIG. 9A shows the results of immunohistological analysis of brain regions showing the presence of HIV-1 p24$^+$ infected cells. RNAScope assay was performed using V-HIV1-Clade-B, an antisense probe, and HIV-1 RNA was detected as a single brown dot or cluster of dots. 200× original magnification.

FIG. 9B shows the results of immunofluorescence staining of mouse astrocytes (GFAP) in HIV-1-infected mouse brain near human microglial cells (HLA-DR$^+$), and HIV-1 p24-positive human microglia. 400× original magnification.

FIG. 9C shows comparison results of viral RNA levels in the brain of CD34-NSG mice and CD34-NOG-hIL-34 mice, which were obtained by semi-nested RT-PCR.

FIG. 9D shows an expression level of each HIV-1 gene in an infected mouse brain. RNAseq reads were aligned to an HIV-1$_{ADA}$ sequence.

FIG. 10A shows the results of staining a paraffin-embedded sagittal section with a 5 μm thickness of brain for human-specific immune cell markers (CD4 and CD8). Images were taken with a Nuance multiplex system at 200× original magnification.

FIG. 10B shows quantification results of human CD4 and CD8 T cells. For HIV-infected mice (n=4) and control mice (n=3), at least 2 sections were counted per mouse. Black bars indicate target mice, and gray bars indicate HIV-infected mice.

FIG. 10C shows a CD4/CD8 ratio. For HIV-infected mice (n=4) and control mice (n=3), at least 2 sections were counted per mouse.

FIG. 12A shows a top list of classical microglial markers expressed in a CD34-NOG-IL-34 mouse brain.

FIGS. 12B and 12C show top rankings of log-fold changes in HIV infection-related genes differentially expressed in HIV-uninfected CD34-NOG-IL-34 and HIV-infected CD34-NOG-IL-34 in human microglia and brain. FIG. 12B shows DEG upregulated with HIV-infected CD34-NOG-IL-34.

FIG. 12C shows DEG downregulated with HIV-infected CD34-NOG-IL-34.

FIG. 12D shows that human genes (261) upregulated in HIV infection are associated with interferon signaling, PRP, and TLR signaling.

FIG. 12E shows that human genes (426) downregulated in HIV infection are closely linked to EIF2 signaling and oxidative phosphorylation pathways.

DESCRIPTION OF EMBODIMENTS

Definition

Figure 1A:
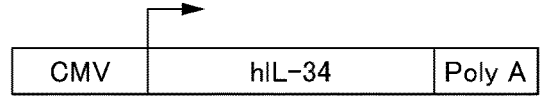
FIGS. 1A to 1D are diagrams showing the production of NOD. Cg-Prkdc$^{scid}$Il2rg$^{tm1Sug}$ Tg (CMV-IL-34) 1/Jic (NOG-hIL-34) mice, and an outline of characterization.
Figure 1B:
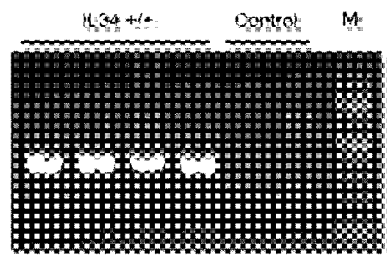
Figure 1C:
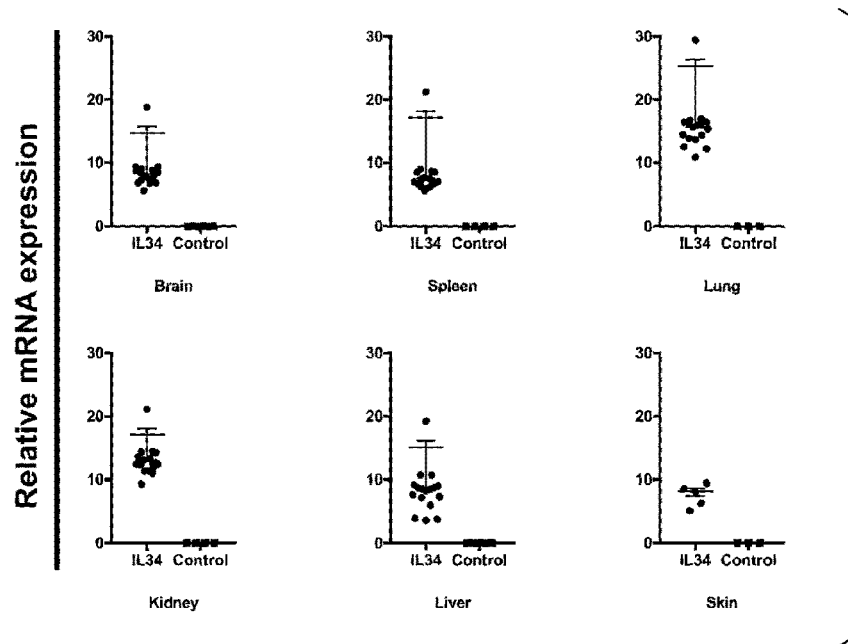
Figure 1D:
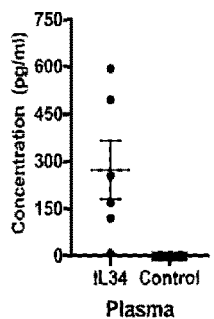
Figure 2:
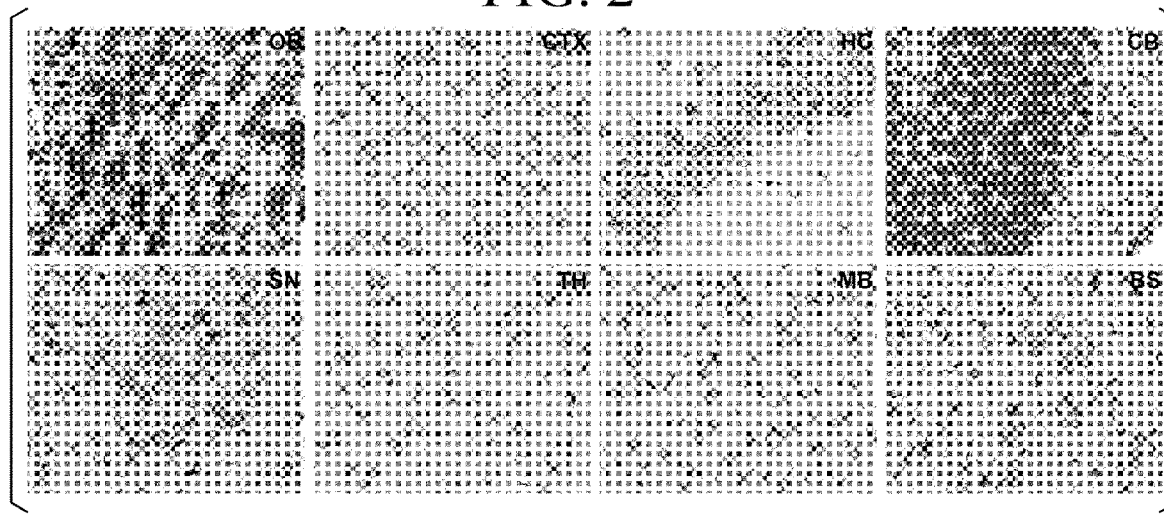
FIG. 2 shows the results of RNAScope assay showing expression of human IL-34 in different regions of a mouse brain. RNAScope assay was performed using Hs-IL-34-NoXMm, an antisense probe targeting 38 to 1774 bp of human IL-34, and human IL-34 was detected as a single brown dot or cluster of dots in brain sections with a thickness of 5 μm. In NOG mice, no signal indicating the presence of human IL-34 was confirmed. 40× magnification.

In the present specification, unless otherwise specified, "IL-34" means an IL-34 protein, and an "IL-34 gene" means a gene encoding the amino acid sequence of IL-34. The term "gene" means a polynucleotide including at least one open reading frame encoding a specific protein, and may include both exons and introns.

In the present specification, "human IL-34 activity" means an activity that induces differentiation of human monocytes and macrophages in the body of a mouse in a case of introduction into an immunodeficient mouse. Human IL-34 activity includes an activity of inducing human microglia from human HSC in the body of an immunodeficient mouse.

In the present specification, sequence identity (or homology) between amino acid sequences or base sequences is obtained as a ratio of matched amino acids or bases to the entire amino acid sequence or the entire base sequence excluding gaps in the obtained alignment by juxtaposing two amino acid sequences or base sequences while inputting gaps in portions corresponding to insertions and deletions so that the corresponding amino acids or bases are most matched. Sequence identity between amino acid sequences or between base sequences can be obtained using various homology search software known in the technical field. For example, a value of sequence identity of amino acid sequences can be obtained by calculation based on alignment obtained by known homology search software BLASTP, and a value of sequence identity of base sequences can be obtained by calculation based on alignment obtained by known homology search software BLASTN.

In the present specification, examples of "stringent conditions" include methods described in Molecular Cloning-A LABORATORY MANUAL THIRD EDITION (Sambrook et al., Cold Spring Harbor Laboratory Press). Examples of stringent conditions include conditions for hybridization by performing incubation at 42 to 70° C. for several hours to overnight in a hybridization buffer consisting of 6×SSC (composition of 20×SSC: 3 M sodium chloride, 0.3 M citric acid solution, pH 7.0), 5×Denhardt's solution (composition of 100×Denhardt's solution: 2% by mass bovine serum albumin, 2% by mass Ficoll, 2% by mass polyvinylpyrrolidone), 0.5% by mass SDS, 0.1 mg/mL salmon sperm DNA, and 50% formamide. As a washing buffer to be used for washing after incubation, a 0.1% by mass SDS-containing 1×SSC solution is preferable, and a 0.1% by mass SDS-containing 0.1×SSC solution is more preferable.

The tem "immunodeficient non-human animal" means a non-human animal having one or more of a lack of functional immune cells such as T cells and B cells; DNA repair defects; defects in reconstitution of genes encoding an antigen specific receptor on lymphocytes; and lack of immune functional molecules such as IgM, IgG1, IgG2a, IgG2b, IgG3, and IgA. An immunodeficient non-human animal may have any of the above or other defects that result in abnormal immune function in the non-human animal.

In the present specification, the phrase "operably linked," which is used with regard to polynucleotides means that a first base sequence is located sufficiently close to a second base sequence, and the first base sequence may affect the second base sequence or a region under control of the second base sequence. For example, the phrase "operably linked to a promoter" means that a polynucleotide is linked to be expressed under the control of the promoter.

In the present specification, the phase a "promoter can function" means that a polynucleotide operably linked to the promoter can be expressed in cells of a target non-human animal.

In the present specification, the term an "expressible state" means that a polynucleotide can be transcribed in a cell into which the polynucleotide has been introduced.

In the present specification, the term an "expression vector" means a vector including a target polynucleotide, which is the vector including a system that enables expression of a target polynucleotide in a cell into which the vector has been introduced.

In the present specification, the term "marker" means a protein that is specifically expressed in a specific type of cell. The "marker" is preferably a protein present on a cell surface.

[Non-Human Animal Having IL-34]

A first aspect of the present invention is a non-human animal having human interleukin-34 (IL-34) in the body thereof.

IL-34 is a type of cytokine that promotes differentiation and survival of monocytes and macrophages via a colony-stimulating factor-1 receptor (CSF1R).

Gene sequences and amino acid sequences of human IL-34 are known, and their sequence information can be obtained from known databases such as GenBank. Examples of gene sequences and amino acid sequences of human IL-34 include the sequences registered as Accession No. NM_152456.2 (SEQ ID NOS: 1 and 2) in GenBank. Human IL-34 is not limited to those having the above sequences, and includes homologs (orthologs, paralogs) and variants thereof.

Human IL-34 includes, for example, the following.

(1) A polypeptide including an amino acid sequence set forth in SEQ ID NO: 2.

(2) A polypeptide consisting of an amino acid sequence in which one or more amino acids have been deleted, substituted, added, or inserted in an amino acid sequence set forth in SEQ ID NO: 2, and having human IL-34 activity.

(3) A polypeptide consisting of an amino acid sequence having 80% or more sequence identity with an amino acid sequence set forth in SEQ ID NO: 2, and having human IL-34 activity.

The human IL-34 gene includes, for example, the following.

(4) A polynucleotide encoding a polypeptide including an amino acid sequence set forth in SEQ ID NO: 2.

(5) A polynucleotide encoding a polypeptide consisting of an amino acid sequence in which one or more amino acids have been deleted, substituted, added, or inserted in an amino acid sequence set forth in SEQ ID NO: 2, and having human IL-34 activity.

(6) A polynucleotide encoding a polypeptide consisting of an amino acid sequence having 80% or more sequence identity with an amino acid sequence set forth in SEQ ID NO: 2, and having human IL-34 activity.

(7) A polynucleotide including a base sequence set forth in SEQ ID NO: 1.

(8) A polynucleotide consisting of a base acid sequence in which one or more bases have been deleted, substituted, added, or inserted in a base acid sequence set forth in SEQ ID NO: 1, and encoding a polypeptide having human IL-34 activity.

(9) A polynucleotide consisting of a base acid sequence having 80% or more sequence identity with a base sequence set forth in SEQ ID NO: 1, and encoding a polypeptide having human IL-34 activity.

(10) A polynucleotide that hybridizes with a polynucleotide consisting of a base sequence set forth in SEQ ID NO: 1 under stringent conditions, and encoding a polypeptide having human IL-34 activity.

In the above (2) and (5), the number of amino acids to be deleted, substituted, added, or inserted is not particularly limited as long as the resulting polypeptide has human IL-34 activity. In the above (8), the number of bases to be deleted, substituted, added, or inserted is not particularly limited as long as the resulting polynucleotide encodes a polypeptide having human IL-34 activity. The number of amino acids or bases to be deleted, substituted, added, or inserted may be, for example, 1 to 80, is preferably 1 to 60, and is more preferably 1 to 50. Examples thereof include 1 to 30, 1 to 20, 1 to 10, 1 to 5, 1 to 3, 1 or 2, and the like.

In the above (3), (6) or (9), the sequence identity is not particularly limited as long as it is 80% or more. The sequence identity is preferably 85% or more, is more preferably 90% or more, is still more preferably 95% or more, and is particularly preferably 97% or more.

In the amino acid sequence set forth in SEQ ID NO: 2, the amino acid sequence of positions 1 to 20 is a signal peptide. Since a signal peptide is cleaved upon extracellular secretion, mature human IL-34 is composed of the amino acid sequence of positions 21 to 242 in the amino acid sequence set forth in SEQ ID NO: 2.

Accordingly, human IL-34 also includes the following.

(11) A polypeptide including an amino acid sequence of positions 21 to 242 in an amino acid sequence set forth in SEQ ID NO: 2.

(12) A polypeptide consisting of an amino acid sequence in which one or more amino acids have been deleted, substituted, added, or inserted in an amino acid sequence of positions 21 to 242 in an amino acid sequence set forth in SEQ ID NO: 2, and having human IL-34 activity.

(13) A polypeptide consisting of an amino acid sequence having 80% or more sequence identity with an amino acid sequence of positions 21 to 242 in an amino acid sequence set forth in SEQ ID NO: 2, and having human IL-34 activity.

The number of amino acids to be deleted, substituted, added, or inserted in the above (12) may be the same as in the case of the above (2). The numerical value of sequence identity in the above (13) may be the same as in the case of the above (3).

Examples of the human IL-34 gene also includes a polynucleotide encoding a polypeptide in which a signal peptide for extracellular secretion is linked to the N-terminal side of the polypeptide of any of the above (11) to (13). The signal peptide is not limited to the signal peptide of human IL-34, and may be a signal peptide of another protein. Examples of such signal peptides include, for example, signal peptides of cytokines other than IL-34.

The non-human animal is not particularly limited as long as it is a non-human animal, but is preferably a mammal. Examples of non-human animals include non-human primates (monkeys, chimpanzees, gorillas, and the like), rodents (mice, rats, guinea pigs, and the like), dogs, cats, rabbits, cows, pigs, horses, goats, sheep, and the like, but examples are not limited thereto. Among them, rodents are preferable and mice are more preferable because they are easily available, and testing thereon is easy.

The non-human animal is preferably an immunodeficient non-human animal since human cells can be engrafted thereto. When the non-human animal is a mouse, immunodeficient mice can be characterized by one or more defects in genes involved in an immune function such as Rag1 and Rag2 (for example, Oettinger, M. A et al., Science, 248: 1517-1523, 1990; Schatz, D. G. et al., Cell, 59: 1035-1048, 1989). Immunodeficient mice can have any of the above or other defects that result in abnormal immune function in the mouse.

Examples of immunodeficient mice include, but are not limited to, NOG mice (NOD. Cg-Prkdc$^{scid}$Il2rg$^{tm1Sug}$/ShiJic), NSG mice (NOD. Cg-Prkdc$^{scid}$Il2rg$^{tm1Wjl}$/SzJ), NOD/ShiJcl mice, and the like. Immunodeficient mice are commercially available, and such commercially available immunodeficient mice can be used without particular limitation.

The non-human animal of the present embodiment is characterized by having human IL-34 in the body. Examples of methods for producing a non-human animal having human IL-34 in the body include a method of administering human IL-34 to a non-human animal, a method of introducing the human IL-34 gene into a non-human animal, a method of transferring cells that secrete human IL-34 into a non-human animal, and the like.

When human IL-34 is administered to a non-human animal, an administration method is not particularly limited as long as human IL-34 is retained in the non-human animal, but parenteral administration is preferable. Examples of routes of parenteral administration include intramuscular injection, subcutaneous injection, intravascular injection, and the like. Administration of human IL-34 may be a single dose or multiple doses, as long as human IL-34 is retained in the non-human animal.

Whether or not a non-human animal has human IL-34 in the body can be confirmed by collecting plasma from the non-human animal and measuring a human IL-34 concentration in the plasma. A method for measuring a human IL-34 concentration in plasma is not particularly limited, but examples thereof include immunochemical methods using anti-human IL-34 antibodies. Examples of such methods include an ELISA method, an EIA method, a RIA method, a Western blotting method, and the like. For measurement of human IL-34 in plasma, a commercially available ELISA kit for measuring human IL-34 or the like may be used.

A concentration of human IL-34 in plasma is, for example, 20 pg/mL or more, is preferably 30 pg/mL or more, is more preferably 50 pg/mL or more, is still more preferably 80 pg/mL or more, and is particularly preferably 100 pg/mL or more. An upper limit of the concentration of human IL-34 in plasma is not particularly limited, and examples thereof include 1000 pg/mL or less, 800 pg/mL or less, or 700 pg/mL or less.

When the human IL-34 gene is introduced into a non-human animal, it is preferable that the human IL-34 be operably linked downstream of a promoter that can function in the non-human animal as an introduction target. Examples of promoters that can function in mammals include a cytomegalovirus (CMV) promoter, an SRα promoter, an SV40 early promoter, an LTR of retrovirus, a Rous sarcoma virus (RSV) promoter, a herpes simplex virus thymidine kinase (HSV-TK) promoter, an EF1α promoter, a metallothionein promoter, a heat-shock promoter, and the like, but examples are not limited thereto.

The human IL-34 gene is introduced into the non-human animal in an expressible state, for example, in the form of an expression vector. The expression vector may contain, in addition to the human IL-34 gene and promoter, control sequences such as enhancers, poly A addition signals, and terminators; and marker genes such as drug resistance genes.

The type of the vector is not particularly limited, and a commonly used expression vector can be used without particular limitation. The vector may be linear or circular, and may be a non-viral vector such as a plasmid, a viral vector (for example, a retrovirus vector such as a lentiviral vector), or may be a transposon vector.

A method for introducing the human IL-34 gene into non-human animals is not particularly limited, and methods generally used for producing transgenic animals can be applied. Examples of methods for introducing a human IL-34 gene into a non-human animal include a method of introducing an expression vector containing the human IL-34 gene into a fertilized egg of the non-human animal as an introduction target by microinjection and the like. When the non-human animal is a mouse, for example, a fertilized egg obtained by mating the NOG mouse (NOD. Cg-Prkdc$^{scid}$Il2rg$^{tm1Sug}$/ShiJic) and NOD/ShiJcl mouse may be exemplified, but examples are not limited thereto.

A fertilized egg into which a human IL-34 gene has been introduced is cultured at 37° C. for about 18 to 24 hours, and then transplanted and implanted in the uterus of a foster mother to allow giving birth to offspring, and thereby a non-human animal having a human IL-34 gene can be obtained.

Whether the non-human animal obtained as described above has a human IL-34 gene or not can be confirmed by extracting genomic DNA from a sample collected from the non-human animal and performing PCR or the like.

In addition, whether the non-human animal expresses a human IL-34 gene or not can be determined by extracting RNA from a sample collected from the non-human animal and performing RT-PCR or the like, or it can be confirmed by performing in situ hybridization and the like using tissue samples collected from non-human animals. Alternatively, it can be confirmed by detecting human IL-34 in a sample collected from the non-human animal using an anti-human IL-34 antibody (for example, an ELISA method, an EIA method, a RIA method, a Western blot method, an EIA method, a RIA method, immunohistological staining, and the like).

A non-human animal into which a human IL-34 gene has been introduced preferably secretes human IL-34. Secretion of human IL-34 by the non-human animal mainly refers to release of human IL-34 from the cells of the non-human animal into the body fluid (blood, tissue fluid, lymph, and the like). Whether or not the non-human animal secretes human IL-34 can be confirmed by measuring a human IL-34 concentration in the plasma collected from the non-human animal. The same examples as described above may be exemplified for a method for measuring the human IL-34 concentration in plasma.

In a case where a cell that secretes human IL-34 (human IL-34-secreting cell) is transferred to a non-human animal, examples of human IL-34-secreting cells include cells derived from human organs and blood, cancer cells, and the like. Examples of cells derived from human organs include cells derived from the spleen, thymus, liver, small intestine, large intestine, prostate gland, lungs, heart, brain, kidneys, testes, uterus, and the like. Examples of cells derived from human blood include blood cells and the like contained in the peripheral blood mononuclear cell fraction. For example, cells secreting human IL-34 can be selected from cell lines established from these human cells, and can be used as human IL-34-secreting cells for transfer to non-human animals. Alternatively, cells of non-human animals into which the human IL-34 gene has been introduced may be used as human IL-34-secreting cells. The cells of the non-human animal are preferably cells of a non-human animal belonging to the same species as the non-human animal to which cells are to be transferred. For example, if the non-human animal to which cells are to be transferred is a mouse, it is preferable that the cells into which the human IL-34 gene is transferred be mouse cells. Non-human animal cells into which the human IL-34 gene is introduced are not particularly limited, but examples thereof include cells derived from organs or blood or cell lines thereof, hematopoietic stem cells (such as CD34-positive hematopoietic stem cells), cancer cells, and the like. Examples of cells derived from the organs and blood of the non-human animals include cells of non-human animals derived from organs and blood fractions similar to those exemplified for the human IL-34-secreting cells. As described above, the human IL-34 gene is introduced into the non-human animal cells in an expressible state, for example, in the form of an expression vector. The method for introducing the human IL-34 gene into non-human animal cells is not particularly limited, and a method generally used as a gene transfer method can be applied. Examples of such methods include viral infection, lipofection, microinjection, calcium phosphate, DEAE-dextran, electroporation, transposon, and particle gun methods, and the like, but examples are not limited thereto.

Whether the human cell line or the human IL-34 transgenic cell secretes human IL-34 can be confirmed by measuring a IL-34 concentration in a culture solution of the cells or cell lines or the human IL-34 transgenic cells. Examples of methods for measuring a human IL-34 concentration in the culture solution include the same as those described above.

The method for transferring human IL-34-secreting cells to non-human animals is not particularly limited, and methods generally used for transferring cells to non-human animals can be applied. Examples of methods for transferring human IL-34-secreting cells to non-human animals include a method of administering human IL-34-secreting cells in the spleen, in the liver, subcutaneously, or intravenously according to the type of cells used, and the like.

A non-human animal transfected with human IL-34-secreting cells preferably secretes human IL-34. Secretion of human IL-34 by the non-human animal mainly refers to release of human IL-34 from the human IL-34-secreting cells transferred to the non-human animal into the body fluid (blood, tissue fluid, lymph, and the like). Whether or not the non-human animal secretes human IL-34 can be confirmed by measuring a human IL-34 concentration in the plasma collected from the non-human animal. The same examples as described above may be exemplified for a method for measuring the human IL-34 concentration in plasma.

In addition, examples of methods for producing a non-human animal of the present embodiment include a method in which a non-human animal is directly inoculated and infected with a virus such as a lentivirus or adenovirus incorporating a human IL-34 gene for secretion of human IL-34. Such method may be included in the methods of introducing the human IL-34 gene into a non-human animal described above.

The non-human animal of the present embodiment is preferably a non-human animal having a human IL-34 gene, and is more preferably a non-human animal secreting human IL-34. When a non-human animal has a human IL-34 gene and secretes human IL-34, examples of a concentration of human IL-34 in plasma include the same concentrations as described above.

<Non-Human Animal Having Human Microglia>

By transplanting human CD34-positive hematopoietic stem cells into a non-human animal having human IL-34, human microglia are induced from the CD34-positive hematopoietic stem cells in the body of the non-human animal. In other words, by transplanting human CD34-positive hematopoietic stem cells into a non-human animal having human IL-34, a non-human animal having human microglia can be produced.

Accordingly, the non-human animal of the present embodiment may be a non-human animal in which human CD34-positive hematopoietic stem cells have been transplanted to a non-human animal having human IL-34. In addition, the non-human animal of the present embodiment may be a non-human animal having human IL-34 and human microglia.

Furthermore, in one embodiment, the present invention provides a method for producing a non-human animal having human microglia, including transplanting a human CD34-positive hematopoietic stem cell into a non-human animal having human IL-34 in the body thereof.

Human CD34-positive hematopoietic stem cells can be obtained from human cord blood, bone marrow, blood, and the like. A method for obtaining human CD34-positive hematopoietic stem cells from these samples is not particularly limited, and examples thereof include a method in which, after density gradient centrifugation of these samples, CD34-positive cells are isolated by a magnetic bead method using an anti-human CD34 antibody. The purity of the obtained human CD34-positive hematopoietic stem cells may be confirmed by flow cytometry or the like.

A method for transplanting human CD34-positive hematopoietic stem cells into a non-human animal is not particularly limited, and methods generally used for transplantation of hematopoietic stem cells can be applied. Examples of methods for transplanting human CD34-positive hematopoietic stem cells into a non-human animal include a method of administering human CD34-positive hematopoietic stem cells into the liver or a vein after whole-body treatment of postnatal non-human animals (for example, postnatal day 0 to 1) with radiation. The number of human CD34-positive hematopoietic stem cells to be transplanted is not particularly limited, but, for example, $10^3$ or more is preferable, and $10^4$ or more is more preferable. An upper limit of the number of human CD34-positive hematopoietic stem cells to be transplanted is not particularly limited, and is, for example, $10^{10}$ or less, $10^9$ or less, $10^8$ or less, and the like.

Whether non-human animals have had human CD34-positive hematopoietic stem cells transplanted thereinto can be determined by analyzing a blood sample or a spleen tissue sample of the non-human animal by flow cytometry and the like using an antibody against a human immune cell marker (CD45, CD3, CD19, CD8, CD14, and the like).

When human CD34-positive hematopoietic stem cells are transplanted into a non-human animal having human IL-34, human microglia are differentiated and induced from CD34-positive hematopoietic stem cells in the non-human animal body, and a non-human animal having human microglia can be obtained. Whether or not a non-human animal has human microglia can be confirmed by immunohistological staining using an antibody against a marker specific for human microglia (for example, double-positive for HLA-DR and Iba1).

In non-human animals having human IL-34, a site where human microglia are present is not particularly limited, but because microglia are usually present in the central nervous system, also in the non-human animal, the human microglia is preferably present in the central nervous system, and more preferably in the brain.

The human microglia possessed by the non-human animal of the present embodiment preferably express at least one gene selected from the group consisting of CD74, b2m, AIF1, CD14, CD68, CSF1R, ITGAM (CD11b), P2RY12, CX3CR1, TREM2, TMEM119, CCL2, TNF, HGH (IL-6), CXCL8, IL-10, IL-1a, CXCL10, PU.1 (SPI1), ETV5, and APOE. These genes are known as markers of classical macrophages/microglia. In addition, it is preferable that human microglia possessed by the non-human animal of the present embodiment express a part or all of the genes described in Tables 2A to 2H to be shown later.

In addition, human microglia possessed by the non-human animal of the present embodiment preferably secrete at least one cytokine selected from the group consisting of CCL2, TNF, HGH (IL-6), CXCL8, IL-10, IL-1a, and CXCL10.

<Non-Human Animal Infected with Human Immunodeficiency Virus>

As shown in the examples below, non-human animals having human IL-34 can have larger numbers of human microglia compared to non-human animals not having human IL-34. For this reason, human immunodeficiency virus (HIV) infection in the human brain can be appropriately simulated by infecting a non-human animal having human IL-34 and human microglia with HIV.

Accordingly, the non-human animal of the present embodiment may be a non-human animal having human IL-34 infected with HIV. Such non-human animal is preferably a non-human animal having human IL-34 and human microglia.

In one embodiment, the present invention also provides a method for producing an HIV-infected non-human animal, the method including producing a non-human animal having human microglia (the non-human animal has human IL-34 and human microglia) according to the method described above, and then infecting the non-human animal having human microglia with HIV.

The HIV used for infection may be either HIV-1 or HIV-2. A method of infection of non-human animals with HIV is not particularly limited, and commonly used infection methods can be applied. Examples of methods of infecting non-human animals with HIV include a method of intraperitoneally administering HIV and the like. A viral load used for infection is not particularly limited as long as HIV infection can be established, but examples thereof include 500 to 5000 $TCID_{50}$, 700 to 3000 $TCID_{50}$ is preferable, and a specific example thereof includes 1000 $TCID_{50}$.

Whether or not HIV infection is established in a non-human animal can be confirmed by measuring an amount of HIV in peripheral blood collected from the non-human animal. For example, when an amount of HIV is detected at about $10^6$ RNA copies/mL in peripheral blood, it can be determined that HIV infection has been established. In addition, HIV infection of the brain can be confirmed by performing immunostaining targeting HIV-specific proteins or RNA, in situ RNA hybridization, or the like in brain tissue sections of the non-human animal. It is preferable that the non-human animal of the present embodiment have HIV infecting the brain.

The non-human animal of the present embodiment can appropriately reconstitute the human hemolymph system by having human IL-34 in the body. In particular, reconstitution of human microglia in the brain, which was difficult in non-human animals such as immunodeficient mice of the related art, becomes possible. For this reason, the non-human animal of the present embodiment can be used to produce a model for infection of a virus such as HIV having microglia as the main reservoir.

The non-human animal of the present embodiment can be used for elucidating the viral infection mechanism targeting microglia, and for screening and evaluating a therapeutic drug for viral infection. In addition, the non-human animal of the present embodiment can be used for elucidating the mechanism of central nervous system diseases mediated by microglia and for screening and evaluating a therapeutic drug.

[Method for Producing Human Microglia]

A second aspect of the present invention is a method for producing human microglia, which includes obtaining human microglia from the non-human animal of the first aspect.

As described above, since the non-human animal of the first aspect can retain many human microglia, it can be used for producing human microglia. Therefore, in one aspect, the present invention provides a method of producing human microglia using the non-human animal of the first aspect, and human microglia obtained by such production method.

The method for producing human microglia of the present embodiment can include the following steps:

a step (a) of administering human IL-34 or introducing a human IL-34 gene into a non-human animal to obtain a non-human animal having human IL-34 in the body;

a step (b) of implanting human CD34-positive hematopoietic stem cells into the non-human animal obtained in the step (a) to obtain a non-human animal having human microglia; and a step (c) of obtaining human microglia from the non-human animal obtained in the step (b).

The steps (a) and (b) can be carried out as described above in the section "[Non-human animal having IL-34]."

The step (c) can be carried out by isolating human microglia from a blood sample or brain tissue of the non-human animal obtained in the step (b). For example, microglia can be isolated from the sample by performing density gradient centrifugation, a magnetic bead method using an antibody against a human microglia specific marker, or the like. In a case where human microglia are isolated from brain tissue, density gradient centrifugation may be performed after suspending and homogenizing brain tissue in an appropriate buffer solution (for example, phosphate-buffered saline, and the like).

Examples of human microglia-specific markers include HLA-DR, Iba1, CD74, b2m, AIF1, CD14, CD68, CSF1R, ITGAM (CD11b), P2RY12, CX3CR1, TREM2, TMEM119, CCL2, TNF, HGH (IL-6), CXCL8, IL-10, IL-1a, CXCL10, PU.1 (SPI1), ETV5, and APOE, but examples are not limited thereto.

The human microglia obtained by the production method of the present embodiment can be used for elucidating the function of human microglia, elucidating the mechanism of virus infection targeting human microglia, evaluating drugs targeting human microglia, and the like.

EXAMPLES

The present invention will be described based on examples. However, the embodiments of the present invention are not limited to the description of these examples. In the following examples, mice are used as non-human animals, but the embodiments of the present invention are not limited to mice. Other materials and methods are not limited to those described in the following examples.

[Method]

<Production of NOG-hIL-34 Mice>

NOG (NOD Cg-Prkdc$^{scid}$Il2g$^{tm1Sug}$/Jic) and NOD/ShiJcl (NOD) were used. NOG mice were bred under specific pathogen-free conditions at the Central Institute for Experimental Animals (CIEA). NOD/ShiJcl mice were purchased from CLEA Japan, Inc. (Tokyo, Japan).

For the production of transgenic NOG mice expressing human IL-34, a linear DNA vector (pCMV6-XL4) containing human IL-34 (hIL-34) cDNA (Origene Technologies, Inc., Rockville, Md., USA) under the control of a CMV-promoter was microinjected into fertilized eggs obtained by crossing NOG mice with NOD mice. Three mice (#11, #13, and #24) among the obtained 26 mice weanlings were positive by polymerase chain reaction (PCR) amplifying hIL-34 cDNA.

<Characterization of NOG-hIL-34 Tg Mice>

(Quantification of Human IL-34 by ELISA)

Transgenic expression of human IL-34 was evaluated by quantifying human IL-34 in mouse plasma (1:10 dilution) using human IL-34 ELISA quantification set (R & D systems, MN, USA) according to the manufacturer's instructions. Absorbance at 450 nm was measured with SpectraMax M3 (Molecular Devices, USA).

(RT-PCR of Human IL-34 Transcripts)

For RNA isolation from spleen, lung, liver, kidney, intestine, skin, and brain tissue, each tissue was homogenized in a Trizol solution using Qiagen Tissue Lyzer II (Valencia, Calif.), and RNA was extracted by a phenol-chloroform method. Synthesis of cDNA from RNA was performed using Verso cDNA Synthesis Kit (Thermo Scientific, Vilnius, Lithuania) according to the manufacturer's instructions, and amplification of cDNA was performed with ABI Step One Plus real-time PCR device (Applied Biosystems, MA, USA) using TaqMan detection chemistry. Expression of human IL-34 (Hs01050926_m1) in samples of humanized NOG-hIL-34 Tg mice was compared to that in samples of humanized mice. Human GAPDH (Hs03929097_g1) was used as a housekeeping gene. Real-time PCR settings were as follows: 40 cycles of 2 minutes at 50° C., 10 minutes at 95° C., and 15 seconds at 95° C.; and 1 minute at 60° C. A fold change in a relative amount of each target gene mRNA to GAPDH was obtained between the humanized NOG-hIL-34 Tg mouse group (transgenic group) and the humanized mouse group (control group). This was performed using a threshold cycle ($C_T$) and 2–$\Delta\Delta C_T$ method ($\Delta C_T = C_T$IL-34-$C_T$GAPDH, $\Delta$ ($\Delta C_T$)=$\Delta C_T$ (transgenic group)–$\Delta C_T$ (control group)).

<Isolation of Human CD34$^+$ HSC>

After obtaining written informed consent from parents and approval from the Institutional Review Board of the University of Nebraska Medical Center (UNMC gynecology and obstetrics department), human CD34+ hematopoietic stem cells were obtained from cord blood of healthy full-term neonates. Cord blood in a leukapheresis medium (MP Biomedicals, Santa, ANA, Calif., USA) was subjected to density-gradient centrifugation at 300 g for 35 minutes. Thereafter, buffy coats were harvested to enrich for CD34$^+$ cells using immunomagnetic beads according to the manufacturer's instructions (CD34$^+$ selection kit; Miltenyi Biotec Inc., Auburn, Calif.). A level of purity of the isolated CD34$^+$ cells was evaluated by flow cytometry. CD34$^+$ HSCs were used as they were, or were stored in liquid nitrogen using a freezing medium containing 50% bovine serum albumin (Sigma-Aldrich, St Louis, Mo., USA), 40% Iscove's modified Dulbecco's medium (GIBCO, Life technologies, Carlsbad, Calif., USA), and 10% dimethyl sulfoxide (DMSO; Sigma-Aldrich St Louis, Mo., USA).

<Transplantation of Human CD34$^+$ HSC>

NOG-hIL-34 Tg mice were bred in a facility under specific pathogen-free conditions (SPF) of the University of Nebraska Medical Center (UNMC). Four hours after the neonatal offspring (0 to 1 days after birth) were irradiated with 1 Gy (RS 2000 X-ray irradiator, Rad Source Technologies, Inc., Suwanee, Ga., USA), the neonatal mice were injected intrahepatically with 1×10$^5$ human CD34$^+$ HSC. A total of 19 human cell-reconstituted animals were used in the following experiments. Engraftment of human leukocytes was examined by analyzing blood samples from facial veins 12 weeks after engraftment using flow cytometry.

<Flow Cytometry>

Blood samples were collected with an ethylenediaminetetraacetic acid (EDTA)-containing tube (BD Microtainer, Franklin Lakes, N.J., USA) from facial veins or by direct cardiopuncture after euthanasia, and centrifuged at 1800 rpm for 8 minutes. Splenocytes were harvested by homogenizing spleen tissue and filtering using a 40 u strainer. Hemocytes and splenocytes were resuspended in a FACS buffer solution (phosphate-buffered saline containing 2% FBS), and incubated for 30 minutes at 4° C. with a cocktail ($CD45^+$ fluorescein isothiocyanate (FITC, BD Biosciences, USA); $CD3^+$ Alexa Fluor 700 (BD, BD Biosciences, USA); $CD19^+$ Brilliant Violet 650 (BD Biosciences, USA); $CD4^+$ allophycocyanin (APC, BD Biosciences, USA); $CD8^+$ Brilliant Violet™ 421 (BV 421, BD Biosciences, USA); and $CD14^+$ PE (BD Biosciences, USA) of antibodies against human immune cell markers. RBCs were lysed by a FACS lysis solution (BD biosciences, USA). Stained cells were washed with a FACS buffer solution and immobilized with 2% paraformaldehyde. Data collection was performed using the acquisition software, FACS Diva v6 (BD Biosciences, USA), implemented on the BD LSR 2 flow cytometer, and data were analyzed using FLOW JO analysis software v 10.2 (Tree Star, USA; www.flowjo.com). Gates were assigned according to the appropriate control population.

<HIV-1 Infection>

Mice in which a human blood-lymphatic system was reconstituted and IL-34 expression was positive (6 to 8 months of age) were intraperitoneally infected with a macrophage-tropic HIV-1 ADA strain (n=12), and were euthanized six weeks after the infection was established.

<Measurement of HIV-1 in Plasma, Spleen, and Brain>

Three weeks and six weeks after infection, the number of viral RNA copies in mouse plasma was obtained using the COBAS Amplicor System v 1.5 kit (Roche Molecular Diagnostics, Pleasanton, Calif., USA). Expression of HIV-1 group-specific antigen (gag) RNA in the brain was analyzed as described above with the ABI Step One Plus real-time PCR device (Applied Biosystems, MA, USA) using TaqMan detection chemistry. Primers and probes used for the second round of PCR were as follows: antisense: 5'-ATCTGGGCCTGGTGCAATAGG-3' (SEQ ID NO: 3); sense: 5'-ACATCAAGCAGCCATGCAAAAT-3' (SEQ ID NO: 4) (Invitrogen, Life technologies, Pittsburgh, Pa., USA); and TaqMan probe: FAM-CATCAATGAG-GAAGCTGCAGAATGGGATAGA-TAMRA (SEQ ID NO: 5) (Applied Biosystems, Foster City, Calif., USA). After normalization of total RNA expression using endogenous mouse GAPDH (Mm9999991515_g1) transcripts, logarithmic changes in RNA expression were calculated using the $\Delta\Delta C_T$ method.

For morphological detection of HIV RNA copies in spleen and brain tissue, RNAScope (Advanced Cell Diagnostics, Hayward, Calif.) was performed according to the manufacturer's instructions. A channel 1 antisense HIV-1 Clade B target probe that contains 78 probe pairs targeting HIV-1 base pairs 854 to 8291 was used. Positive expression was indicated by the presence of brown spots in infected cells. A tissue immunohistochemistry test was performed on HIV-1 p24 (1:20; Dako, Carpenteria, Calif., USA), CD4 (1:100; Abeam, Cambridge, Mass., USA), CD8 (1:100; Abeam, Cambridge, Mass., USA), and HLA-DR (1:100; Novus Biologicals, Littleton, Colo., USA) using EXPOSE Mouse and Rabbit Specific HRP/DAB Detection IHC Kit (Abeam, Cambridge, Mass., USA) according to the manufacturer's instructions.

<Immunohistochemical Analysis>

Tissue (spleen, lung, liver, kidney, heart, skin, and left hemisphere of brain) was immobilized with 4% paraformaldehyde for 24 hours at room temperature, and then embedded in paraffin. Antigen retrieval of paraffin-embedded tissue sections with a 5 μm thickness was performed using Declere/trilogy Solution (Sigma-Aldrich, St Louis, Mo., USA) according to the manufacturer's instructions. An immunohistochemistry test was performed using the EXPOSE Mouse and Rabbit Specific HRP/DAB Detection IHC Kit (Abeam, Cambridge, Mass., USA) according to the manufacturer's instructions. Primary antibodies used were as follows: HLA-DR (1:100; Novus Biologicals, Littleton, Colo., USA), CD14 (1:500; Abeam, Cambridge, Mass., USA), CD68 (1:100; specific to humans, Dako, Carpenteria, Calif., USA), CD163 (1:100; Thermoscientific, Rockford, Ill., USA), CD68 (1:100; specific to mice, LifeSpan Biosciences, Inc., Seattle, Wash., USA), and Iba-1 (1:500; Wako life sciences, Richmond, Va., USA). Nuclei were counterstained with Mayer's hematoxylin, and bright field images were taken using 20× and 40× objective lenses by Nuance Multispectral Tissue Imaging system (CRi, Woburn, Mass.). For quantification, HLA-DR stained sections were scanned using a high-resolution scanner (Ventana Medical Systems, Inc., Oro Valley, Ariz., USA). HLA-DR stained brain sections were analyzed using DEFINIENS Tissue Studio (registered mark) software (Definiens AG, Munich, Germany; www.definiens.com/).

<RNAScope>

For the detection of human IL-34, RNAScope (Advanced Cell Diagnostics, Hayward, Calif.) was performed. Channel 1 antisense Hs-IL-34-No-XMm containing 20 probe pairs targeting positions 38 to 1774 of human IL-34 was used for single-plex chromogenic assay. Briefly, deparaffinized and dehydrated formalin-fixed paraffin-embedded (FFPE) brain sections with a 5 μm thickness were pretreated in a HybEZ hybridization oven for 10 minutes at room temperature with hydrogen peroxide, 8 minutes at 100° C. with a target recovery solution, and 15 minutes at 40° C. with protease IV. Hybridization with the target probe, pre-amplification, amplification, and chromogenic detection using DAB were performed in the HybEZ oven at 40° C. according to the manufacturer's instructions. Positive expression was indicated by the presence of brown spots in cells.

<Immunofluorescent Staining>

For immunofluorescent staining of paraffin-embedded tissues, sections were processed to suppress non-specific adsorption of antibodies with 1× Tris-buffered saline containing 0.5% Tween containing 10% normal goat serum. Primary antibodies were as follows: mouse (Ms) anti-human HLA-DR (1:100; Novus Biologicals, Littleton, Colo., USA); HIV-1 p24 (1:20; Dako, Carpenteria, Calif., USA); anti-synaptophysin (1:800; H. Abeam Cambridge, Mass., USA); rabbit (Rb) anti-MAP2 (1:500; Millipore, Burlington, Mass., USA); Rb anti-Neurofilament H (1:400; Millipore, Burlington, Mass., USA); polyclonal Rb anti-glial fibrillary acidic protein (1:1000; Dako, Carpenteria, Calif., USA); and Rb anti-Iba1 (1:500; Wako life sciences, Richmond, Va., USA). Secondary antibodies were as follows: Alexa Fluor 488-conjugated goat anti-Rb IgG (1:200; Invitrogen, Grand Island, N.Y., USA), and Alexa Fluor 594-conjugated goat anti-Ms IgG (1:200; Invitrogen). Images were taken at 63× using a Zeiss LSM 710 confocal system (Carl Zeiss Microscopy, Jena, Germany) for immunofluorescence imaging.

Representative sagittal sections from mice (n=3) for which double immunostaining of Iba1 and HLA-DR was performed were used to quantify the number of human microglial cells. Using the Nuance Multispectral Tissue Imaging system (CRi, Woburn, Mass.), at a magnification of 400×, a minimum of 2 to 4 selected fields of view of the same brain area were counted for Iba$^+$HLADR$^+$ (human microglia) and Iba1$^+$ (mouse microglia).

<Next-Generation Sequencing>

For sequencing, the frontal cortex of brain tissue (four uninfected humanized transgenic mice, four HIV-1-infected transgenic mice, and four NOG non-humanized control mice) was rapidly frozen in liquid nitrogen and stored at $-80°$ C. Tissue RNA was subjected to RNA cleanup using RNeasy mini columns, and DNase was removed using RNase-free DNase set (Qiagen, Calif., USA). After analysis of nucleic acid integrity, the sample was deep-sequenced at 100 bp/read, <40 million read/sample using Illumina HiSeq 2500 Sequence Analyzer (Illumina, Inc., San Diego, Calif., USA). Reads were trimmed using the fqtrim (ccb.jhu.edu/software/fqtrin/) software to remove ambiguous bases from the reads. Before and after trimming, quality was evaluated for each sample using FASTQC. Reads were aligned to mouse reference genome, GRCm38. p3 (https://uswest.ensembl.org/index.html) by STAR-2.5.3a (https://github.com/alexdobin/STAR) using default parameters, and then quantified by RSEM 1.2.21 (deweylab.github.io/RSEM/) using Ensemble annotations. The abundance of genes and transcripts was measured as Transcripts Per Kilobase Million (TPM) values. The TPM was calculated in consideration of the sequence depth in order to more easily compare a percentage of reads mapped to the gene for each sample after normalizing the length of the gene. The same pipeline was used to further align reads unmapped for the humanized NOG-hIL-34 sample with respect to the human reference genome GrCh37 (uswestensembl.org/index.html), and comparative analysis was performed between uninfected samples and HV-infected samples. Reads that did not match human were further aligned to the HIV genome using STAR and quantified by RSEM. Count and expression data were filtered to exclude genes that do not encode proteins. A subset of these filtered genes was used for (1) analysis of differential expression of various genes between sample groups in R statistical software environment using the package of Bioconductor, (2) identification of pathways using Ingenuity pathway analysis (www.qiagenbioinformatics.com), and (3) analysis of biological processes and molecular functions using Gene Analytics (ga.genecards.org/).

<Statistical Analysis>

Data were analyzed and plotted using GraphPad prism 7 (Graphpad, USA), and expressed as mean±standard error of the mean (SEM). For transcriptome analysis, the data obtained are expressed as the mean±standard deviation of each group. Student's t test was performed using the package of R/Bioconductor. Benjamini-Hochberg (BH) adjusted p-values were calculated by adjusting a false discovery rate (FDR) by multiple tests. $p<0.05$ was perceived to indicate a statistically significant difference.

[Results]

By introducing a vector (NOD. Cg-Prkdc$^{scid}$Il2rg$^{tm1Sug}$) containing the hIL-34 transgene (Tg) under the control of a CMV promoter into NOG mice, human IL-34 transgenic mice (NOD. Cg-Prkdc$^{scid}$Il2rg$^{tm1Sug}$Tg (CMV-IL34) 1/Jic) were developed with a NOG$^{CIEA}$ background. NOG-hIL-34 mice were identified by amplifying hIL-34 (358 bp) transcripts by PCR analysis of ear DNA. Expression of IL-34 in mouse tissues including brain was confirmed by analysis by RT-PCR, ELISA, and RNAscope (FIGS. 1A to 1D and FIG. 2). Humanization of NOG-hIL-34 mice followed a standard method of intrahepatic transplantation of human CD34$^+$ HSCs at the time of birth (CD34$^-$NSG).

Figure 3A:
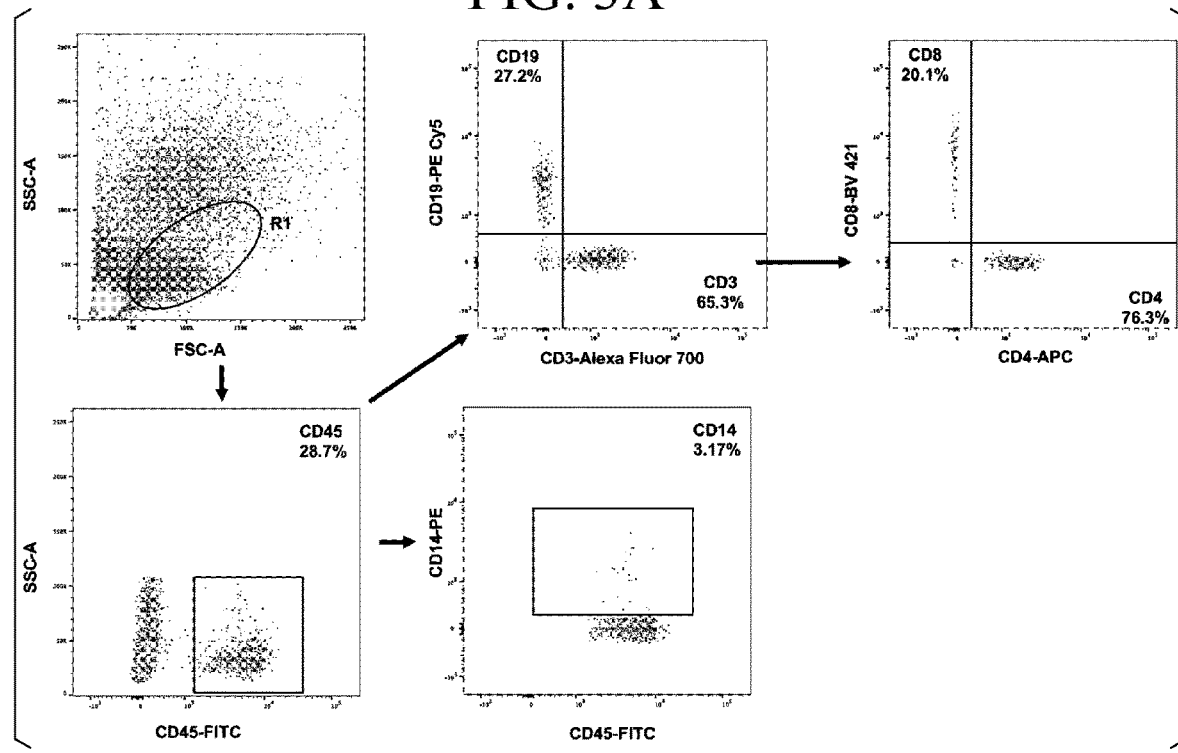
FIGS. 3A to 3B show differentiation and proliferation of human peripheral blood lymphocytes in CD34-NOG-hIL-34 mice.
Figure 3B:
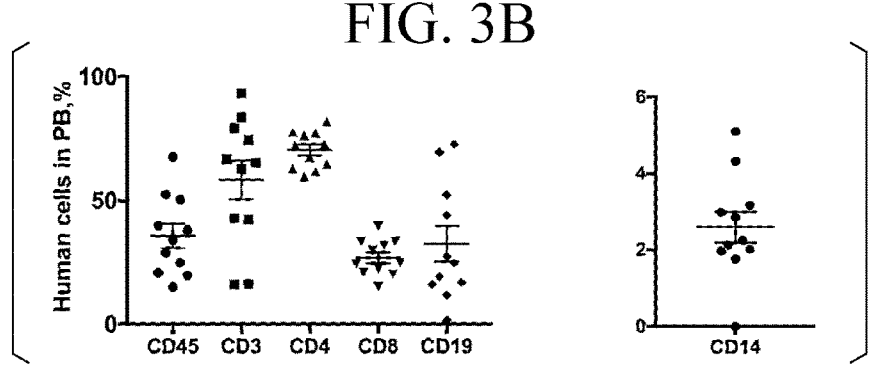
Figure 4A:
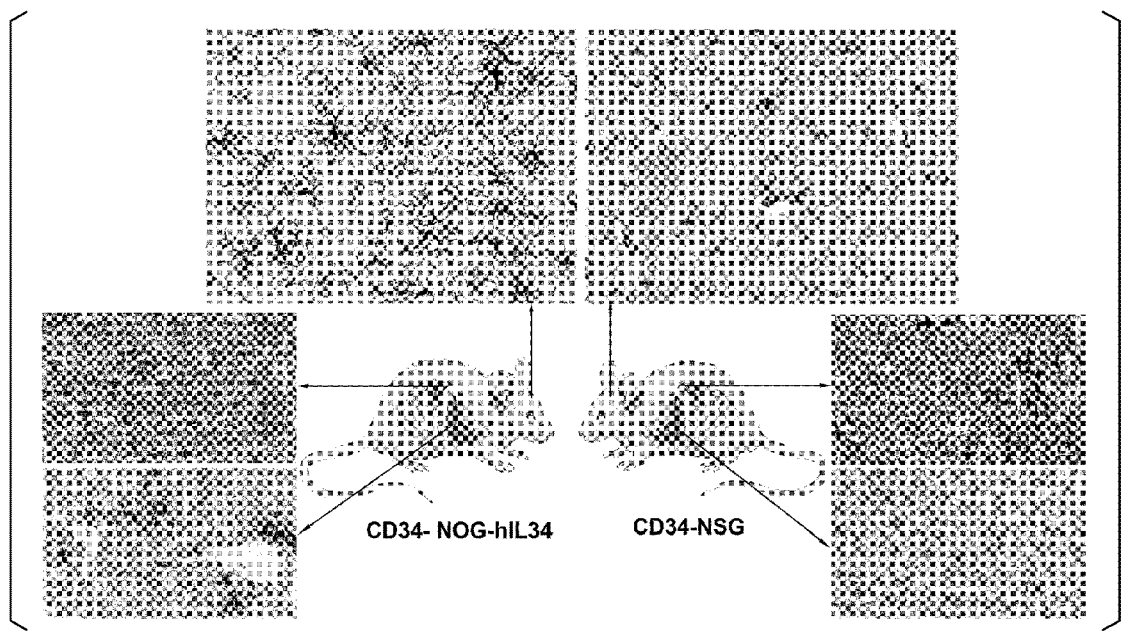
FIGS. 4A to 4F show the presence of human microglial cells in the brains of CD45-NOG-hIL-34 mice.
Figure 4B:
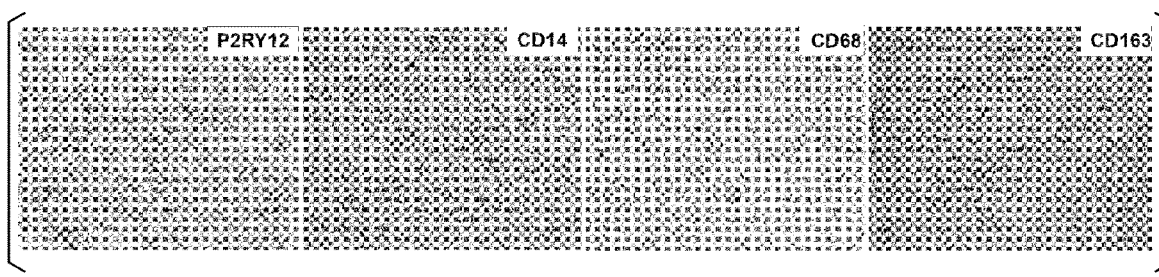
Figure 4C:
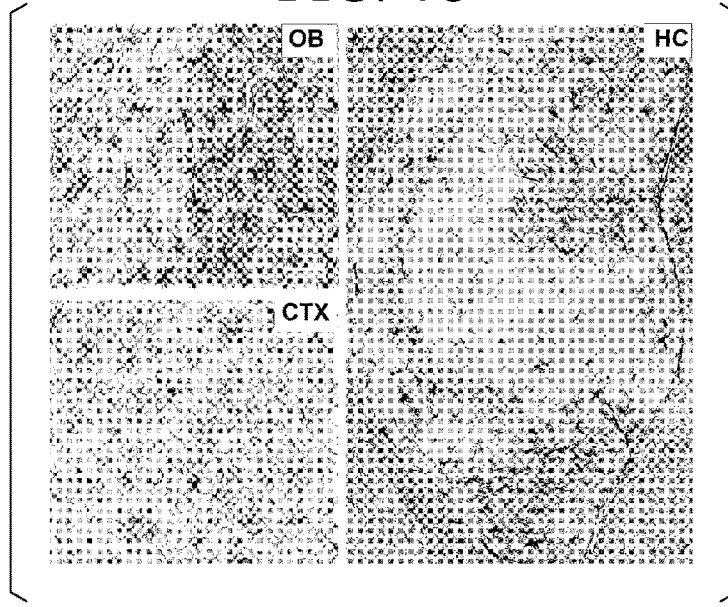
Figure 4D:
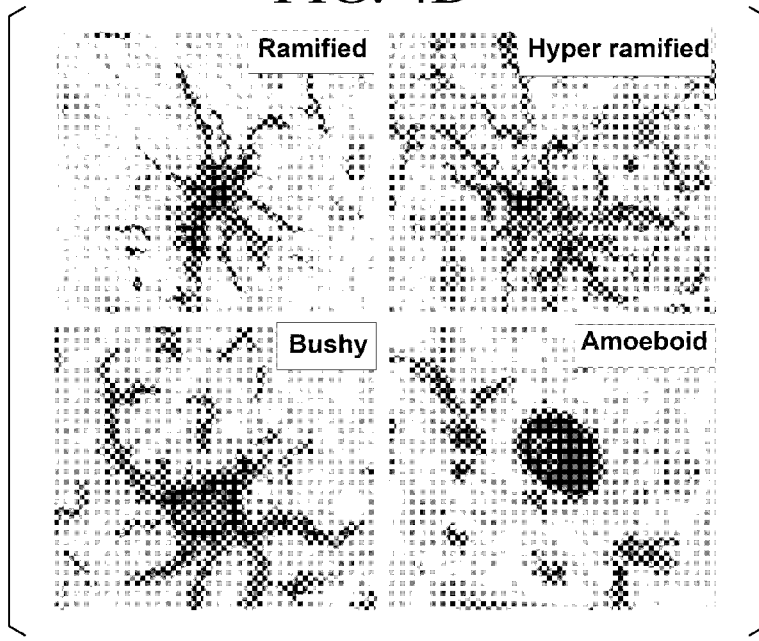
Figure 4E:
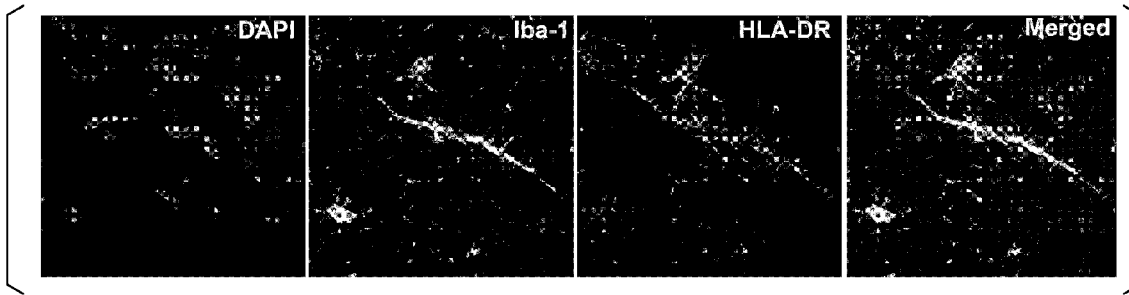
Figure 4F:
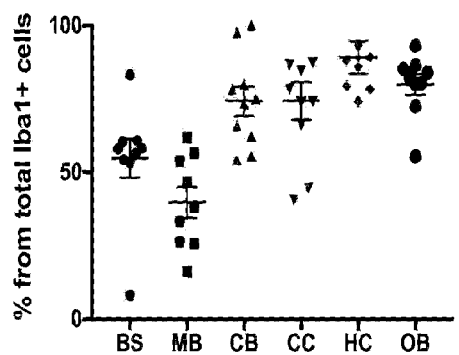
Figure 5A:
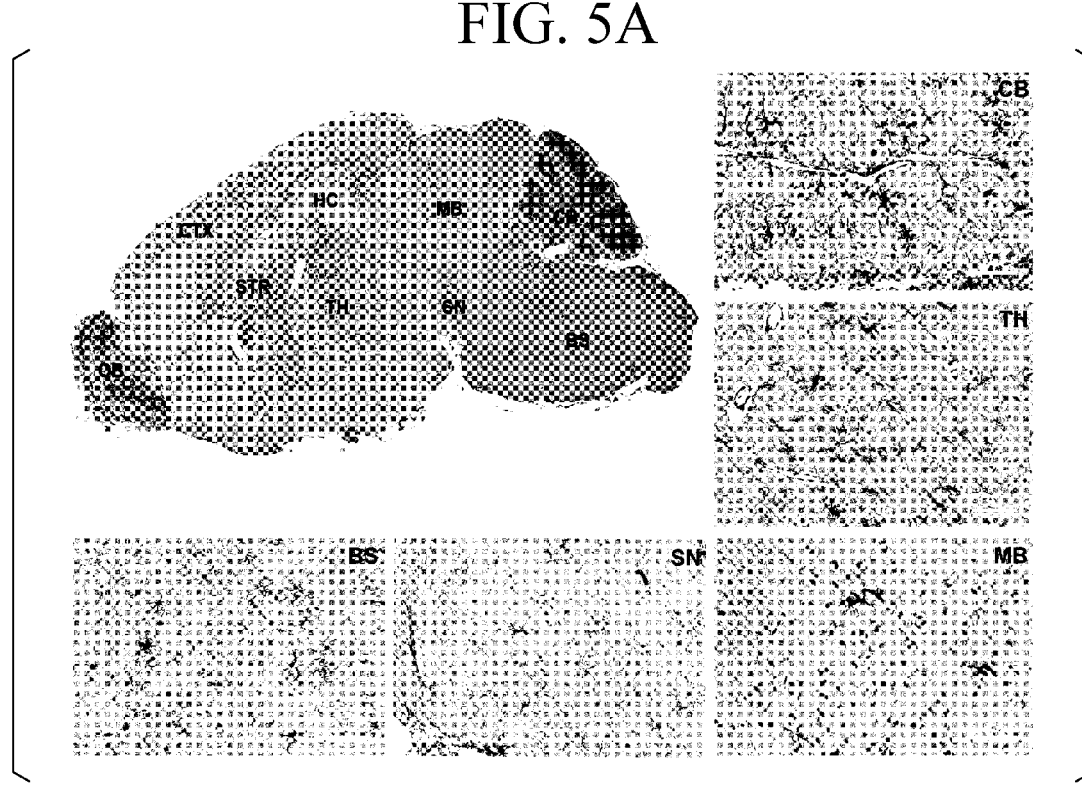
FIGS. 5A to 5B show the reconstitution of human microglia in a mouse brain. Paraffin-embedded brain sections with a thickness of 5 μm were stained for HLA-DR.
Figure 5B:
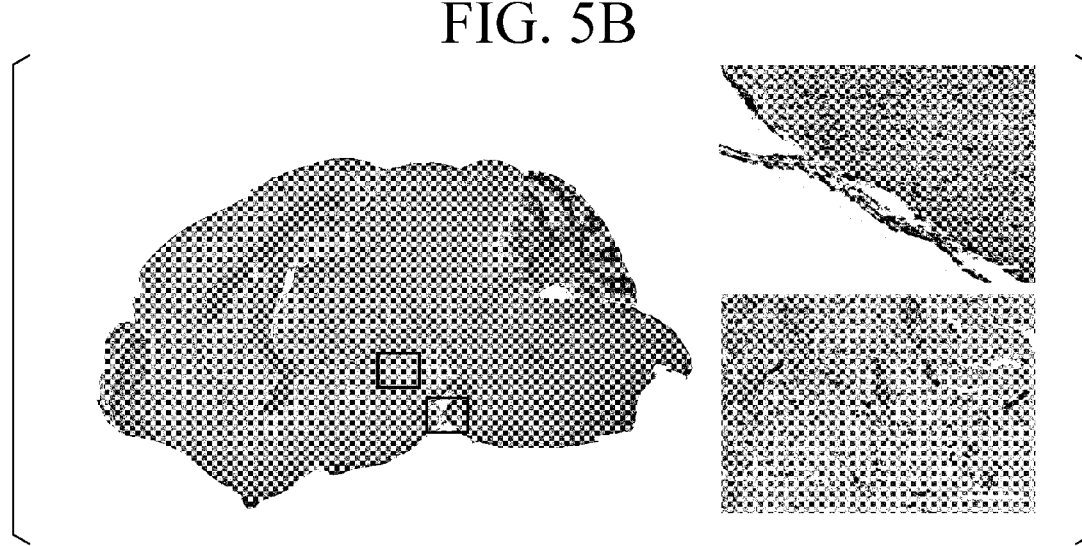
Figure 6:
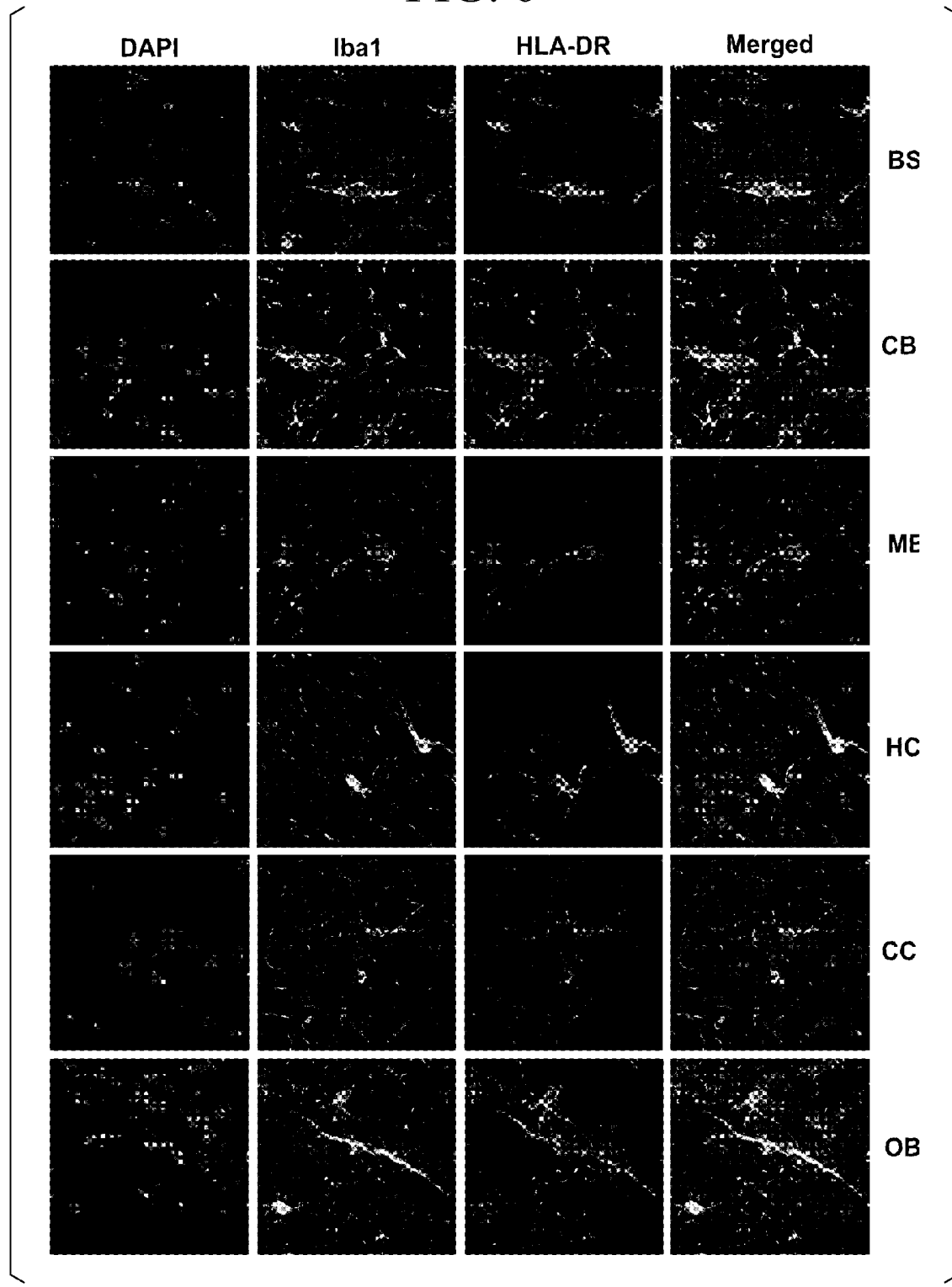
FIG. 6 shows the distribution of human and mouse glial cells in the mouse brain. Sagittal sections of paraffin-embedded brain tissue stained for human MHC class II (HLA-DR) and microglial cells (Iba-1) are shown. Original confocal images were collected with a Zeiss 710 system at 630× magnification.
Figure 7:
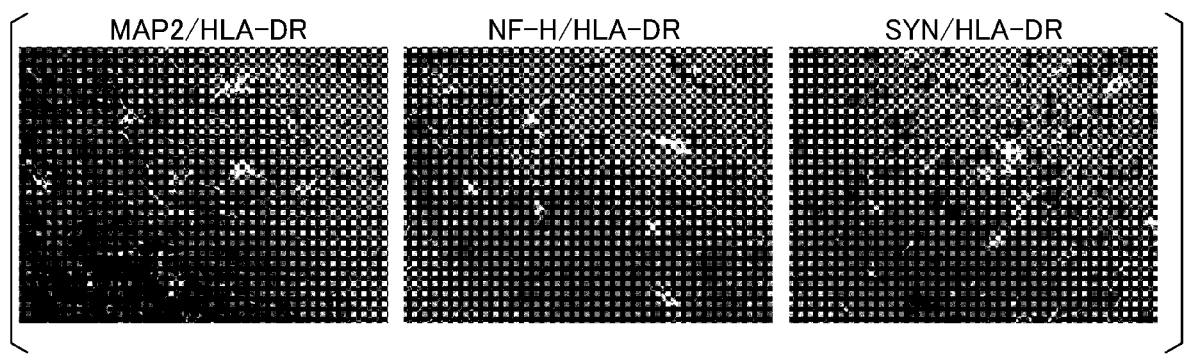
FIG. 7 shows the interaction of mouse neural cells with human microglial cells. Sagittal sections of paraffin-embedded brain tissue stained for human MHC class II (HLA-DR) and mouse neuron marker (MAP-2), neurofilament H (NF-H) or synaptophysin (SYN) are shown. 400× original magnification.
Figure 8A:
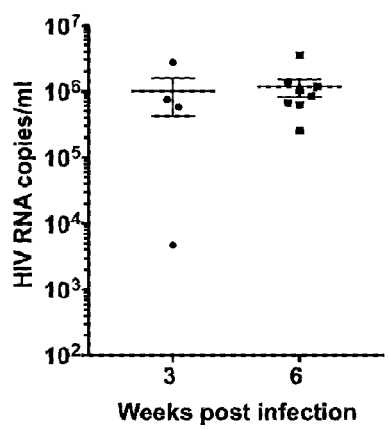
FIGS. 8A to 8D show establishment of systemic HIV infection in CD34-NOG-hIL-34 mice.
Figure 8B:
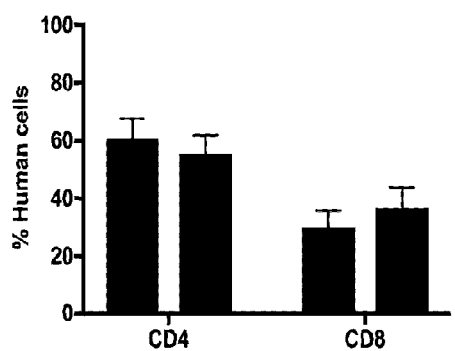
Figure 8C:
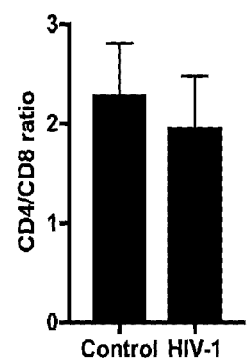
Figure 8D:
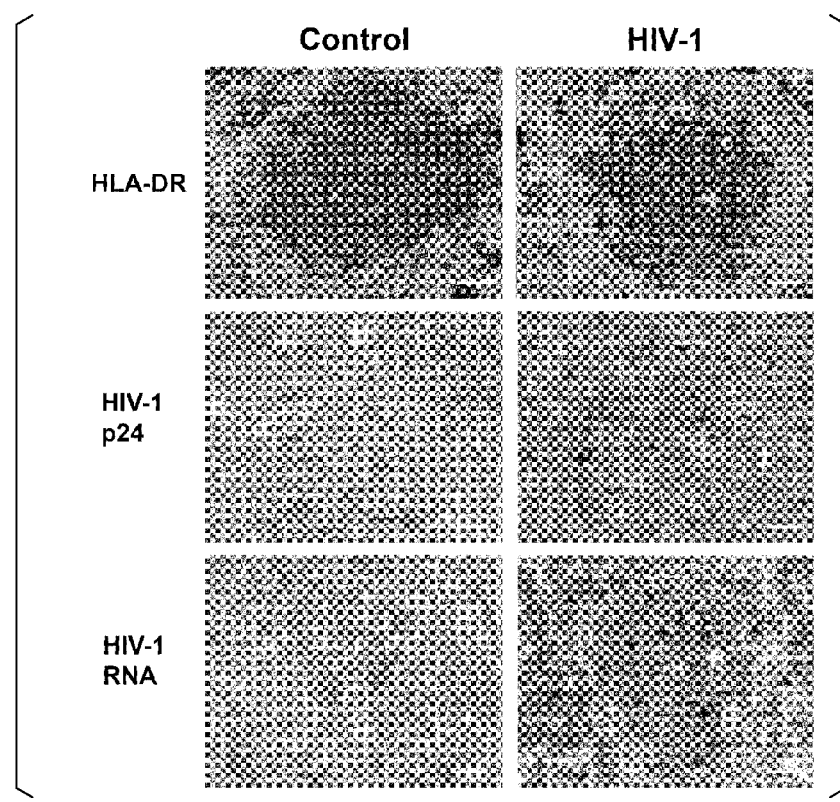

In CD34-NOG-hIL-34 mice, as in the case of CD34-NSG, stable engraftment of the human immune system consisting of human lymphocytes and bone marrow cells was achieved (FIG. 3). Surprisingly, it was recognized that, in the brains of CD34-NOG-hIL-34 mice, the number of human cells having a microglia morphology in which HLA-DR, CD14, CD163, CD68, and P2RY12 were positive significantly increased as compared to human CD34-NSG mice in which such cells were nearly present (FIG. 4A, FIG. 4B, and FIG. 5). Human microglia-like cells were recognized from 4 months of age (data indicates 6 months of age). Human microglia were widely distributed throughout the mouse brain area (FIG. 4C and FIG. 5). Although different types of human microglia were found, most of them were branched microglia, and some were microglia having immature compact amoeba-like forms (FIG. 4D). A percentage of human microglia in the total microglia population was calculated by counting HLA-DR$^+$/Iba1$^+$ double-positive human microglia and Iba1$^+$ mouse microglia, and a percentage of human microglia was a maximum of 80% of total microglia in certain brain areas (FIG. 4E, FIG. 4F, and FIG. 6). A percentage of HLA-DR$^+$/Iba1$^+$ positive cells was high in the olfactory bulb (OB, 59.3±15.4%), cortical area (CTX), striatum (STR), and hippocampus (HC, 48.3±34.2%); and was low in the brain stem ((BS, 28.4±12.5%)) and in the midbrain (MB, 29.5±15.7%). Interaction of the mouse CNS with human microglia showed normal astrocyte behavior and neuronal integrity (FIG. 7).

Figure 9A:
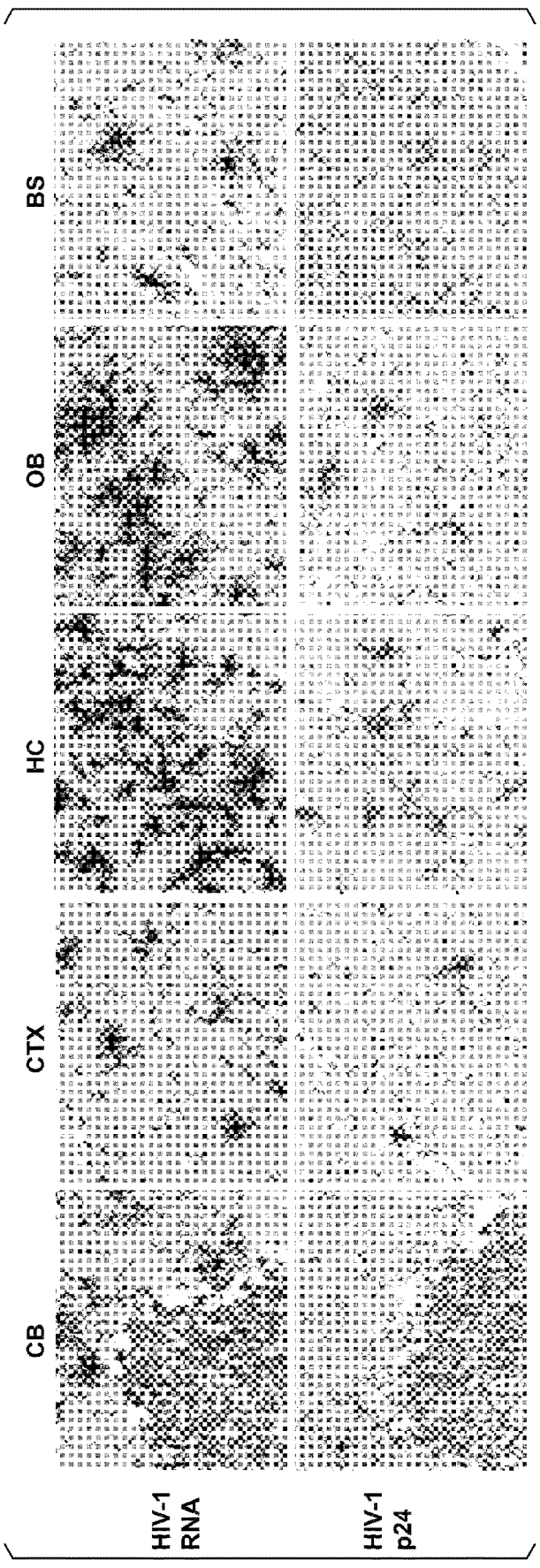
FIGS. 9A to 9D show HIV infection in a humanized mouse brain.
Figure 9B:
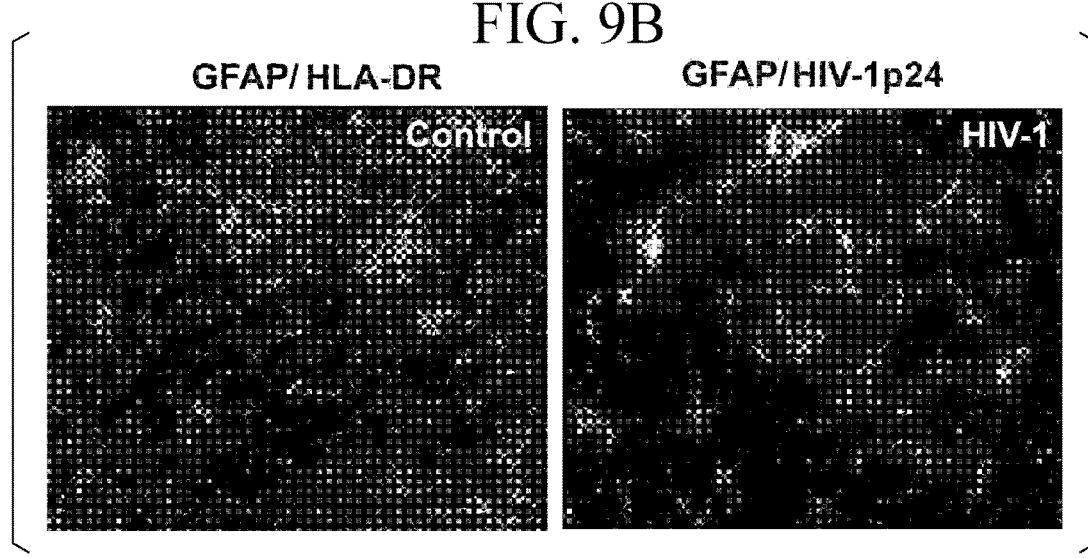
Figure 9C:
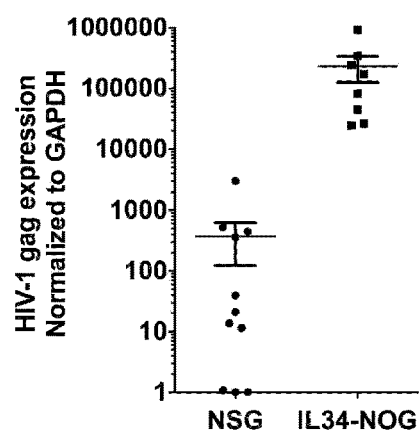

Next, when mice were infected with HIV-1 by intraperitoneal injection of 1000 TCID$_{50}$ virus, a viral load reached $10^6$ RNA copies/mL, in peripheral blood (FIGS. 8A to 8D). Strong infection to human microglia was easily detected in the brain (FIG. 9A, FIGS. 10A to 10C, and FIG. 11). Infected cells were found in several mouse brain areas, and the largest number of infected cells was found in OB, HC, and CTX. By RNAscope technology, it was possible to clearly see infected human cells and extracellular virus particles released from the infected cells. Reactive astrocytic cells were easily detected in the HIV-infected microglia or at the vicinity thereof (FIG. 9). The brains of CD34-NOG-hIL-34 mice had a HIV virus load of 3 to 4 $\log_{10}$-fold ($10^6$ vs. $10^2$) higher than that of the CD34-NSG model which was reconstructed with a human immune system having a comparable viral load in the periphery (FIG. 9C and Table 1).

TABLE 1

|  | Mouse numbers | HIV-1 RNA |
| --- | --- | --- |
| 6 weeks | 3475 | 810600 |
|  | 3476 | 333900 |
|  | 3478 | 190680 |
|  | 3479 | 310800 |
|  | 3473 | 703500 |
|  | 3485 | 378000 |
| 3 weeks | 3463 | <20 |
|  | 3464 | 2184 |
|  | 3474 | 1646 |
|  | 3471 | 8841 |
|  | 3469 | 220500 |
|  | 3467 | <20 |

Figure 9D:
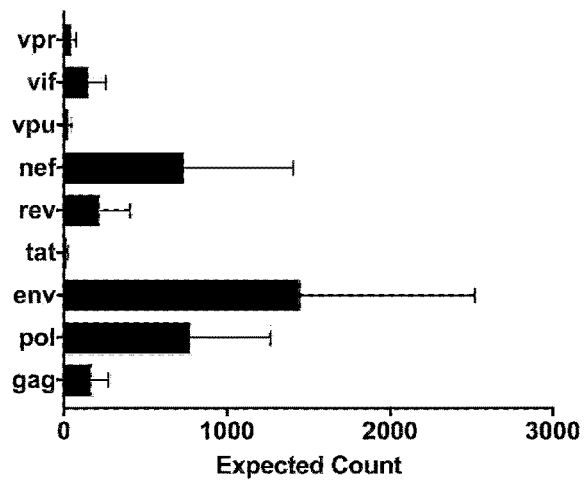
Figure 10A:
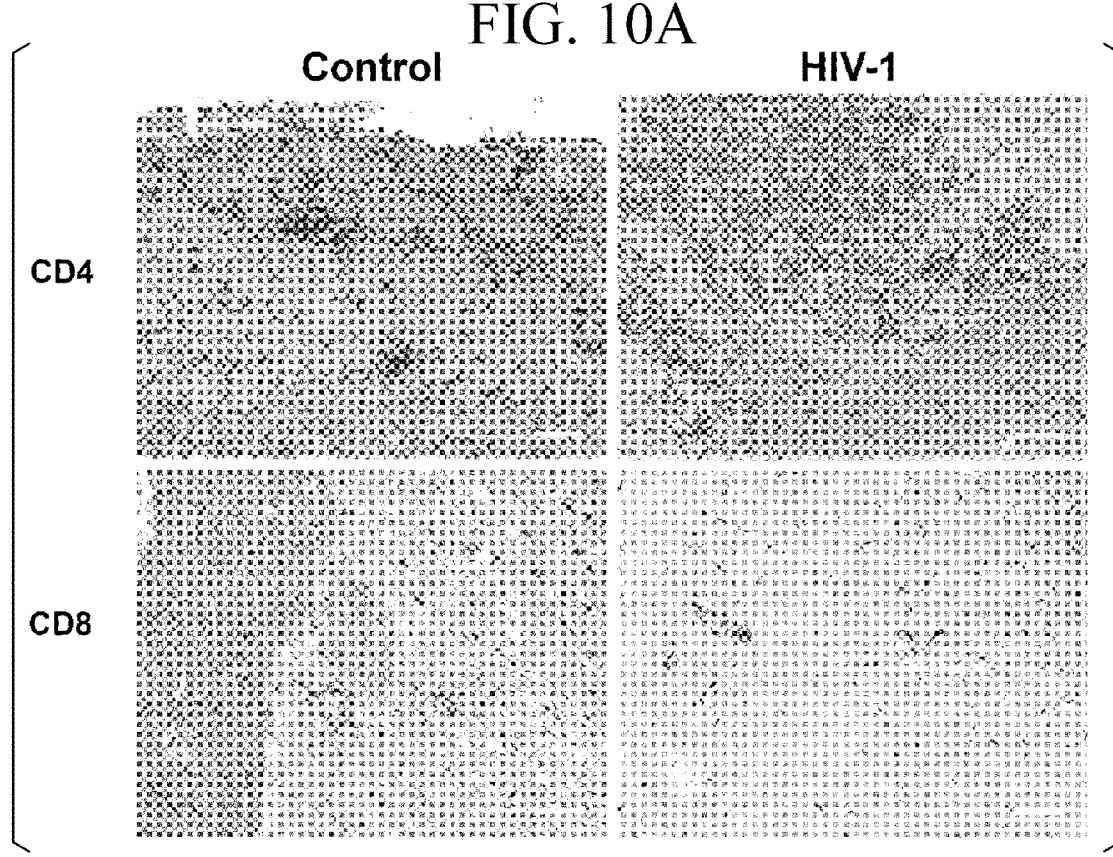
FIGS. 10A to 10C are diagrams showing the distribution of human immune cells in HIV-infected humanized NOG hIL-34 mice.
Figure 10B:
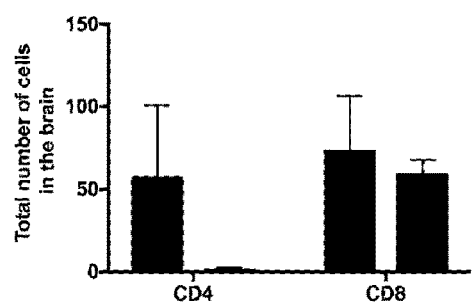
Figure 10C:
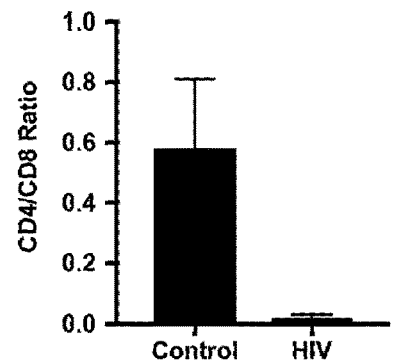
Figure 11:
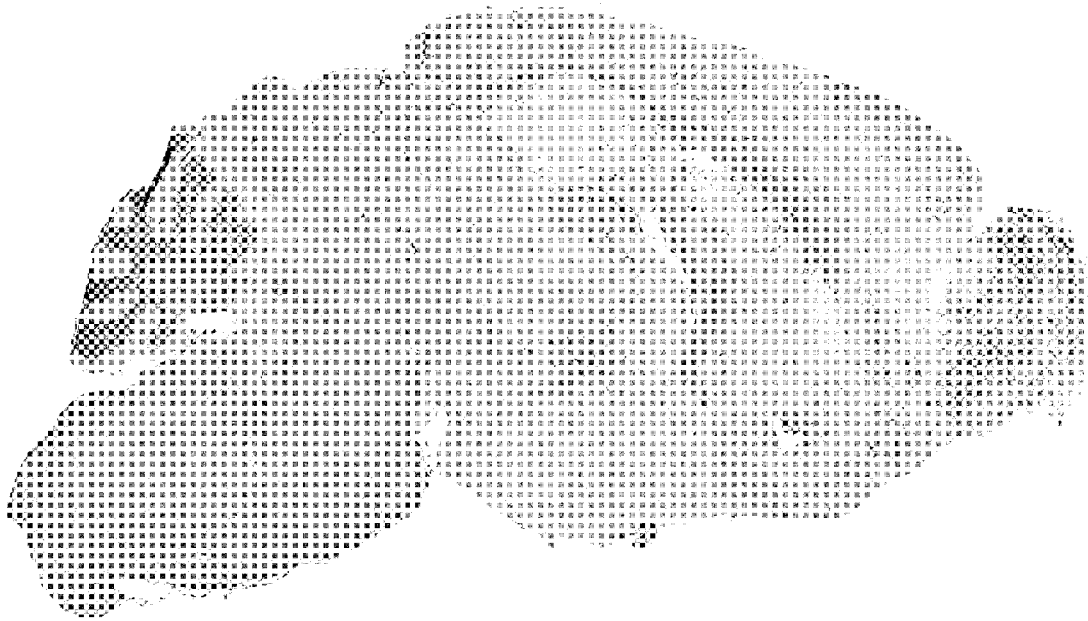
FIG. 11 shows a representative CD34-NOG-hIL-34 mouse brain showing an overview of HIV-1 infection across a mouse brain area stained for HIV-1 p24. The image was taken at 2× magnification 2.
Figure 12A:
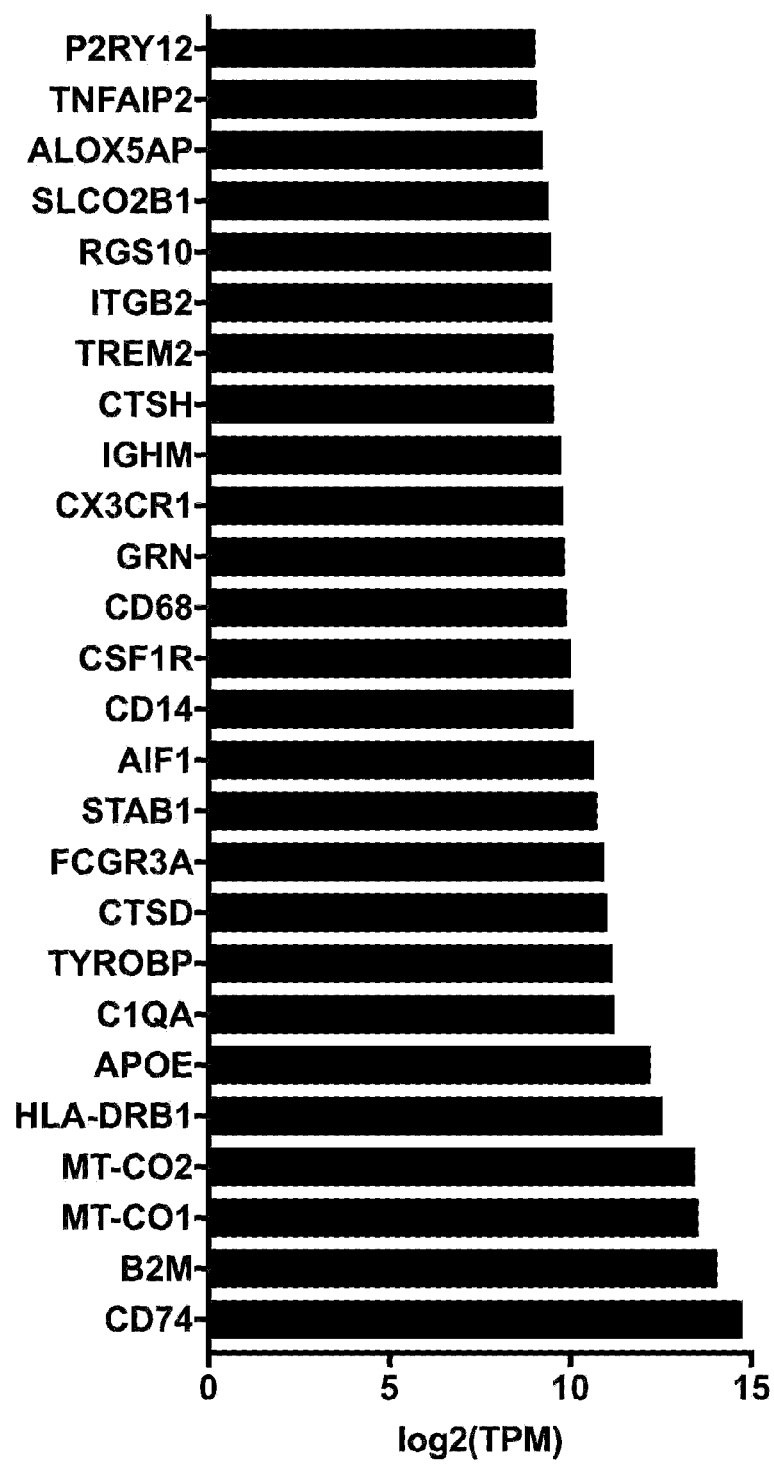
FIGS. 12A to 12E show changes in transcripts in CD34-NOG-hIL-34 brain tissue. Differentially expressed genes (DEG) having p<0.05 in Transcripts Per Kilobase Million (TPM) values are shown. 687 DEG human genes were found by alignment of the gene to the human genome (h19) by comparing uninfected CD34-NOG-hIL-34 mice to infected CD34-NOG-hIL-34 mice. Among them, 261 genes were upregulated by HIV infection, and 426 genes were downregulated by HIV infection.
Figure 12B:
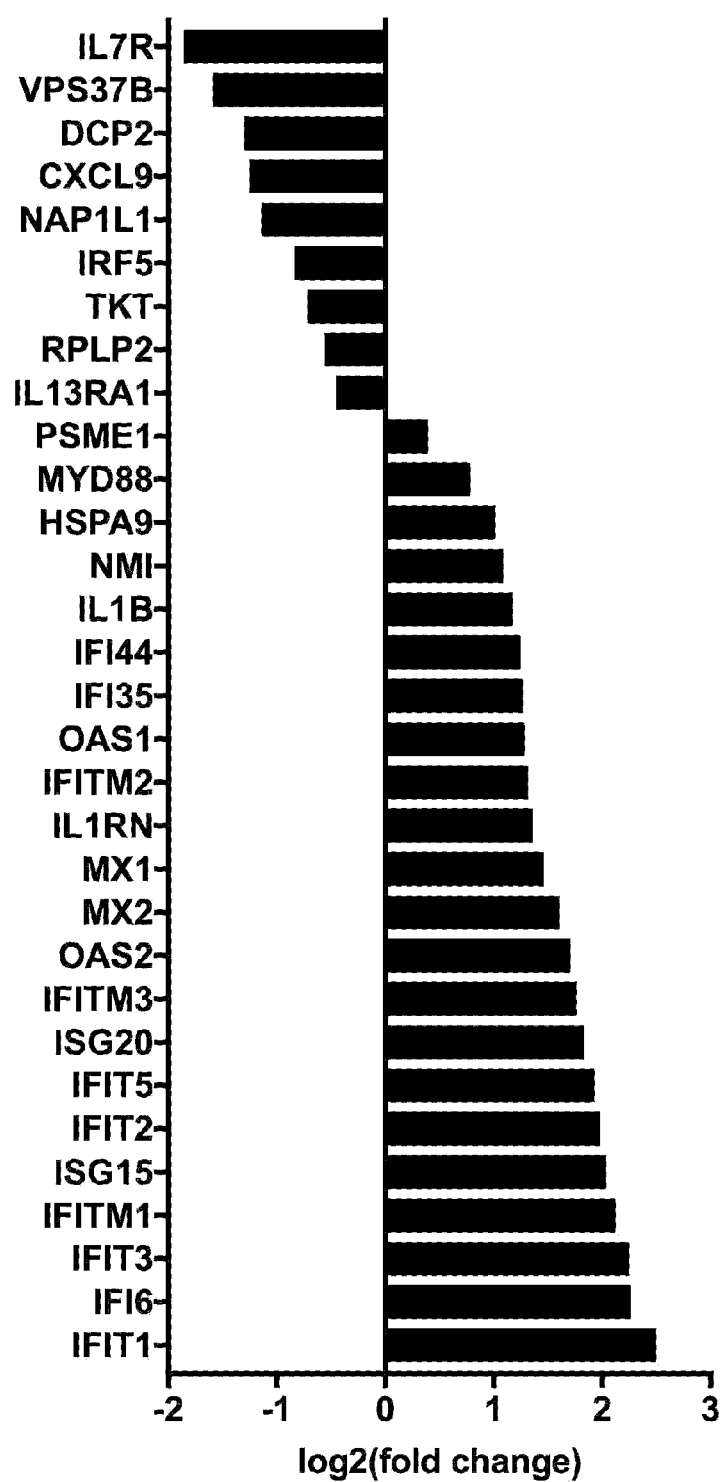
Figure 12C:
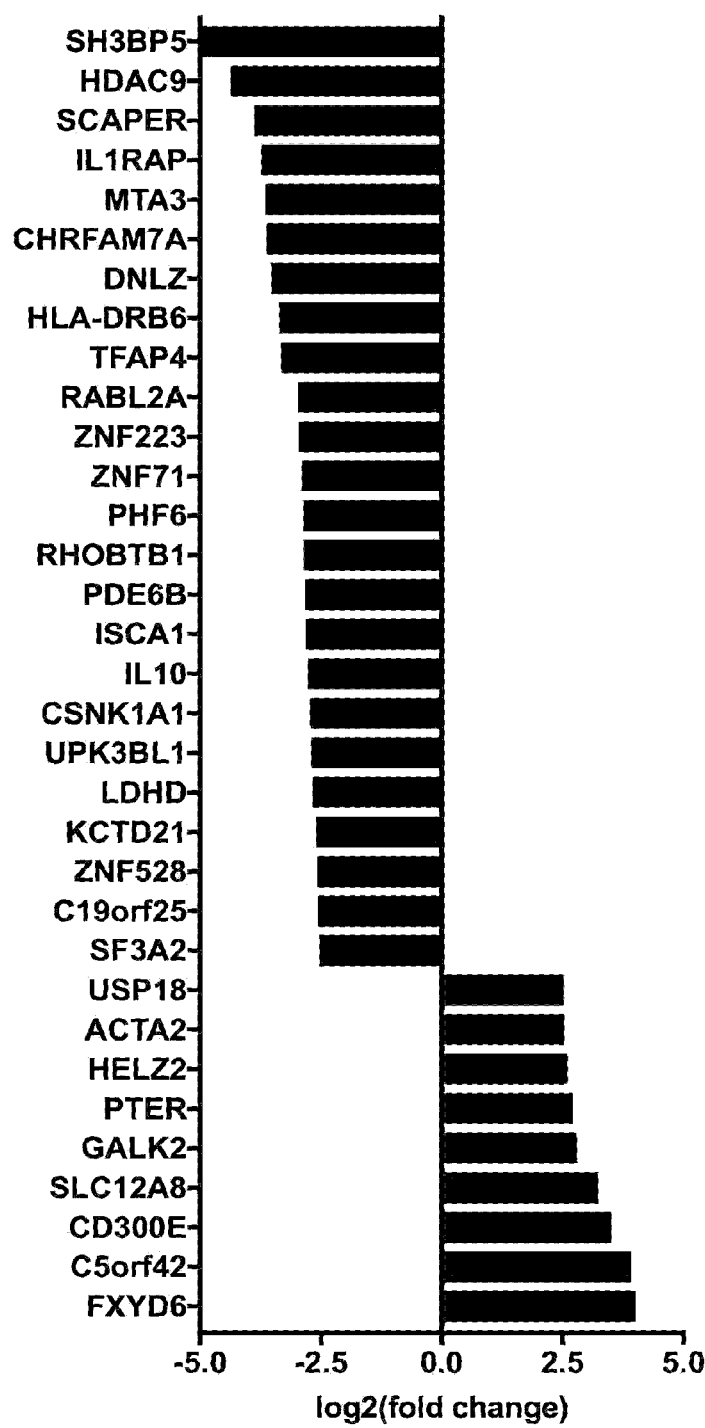
Figure 12D:
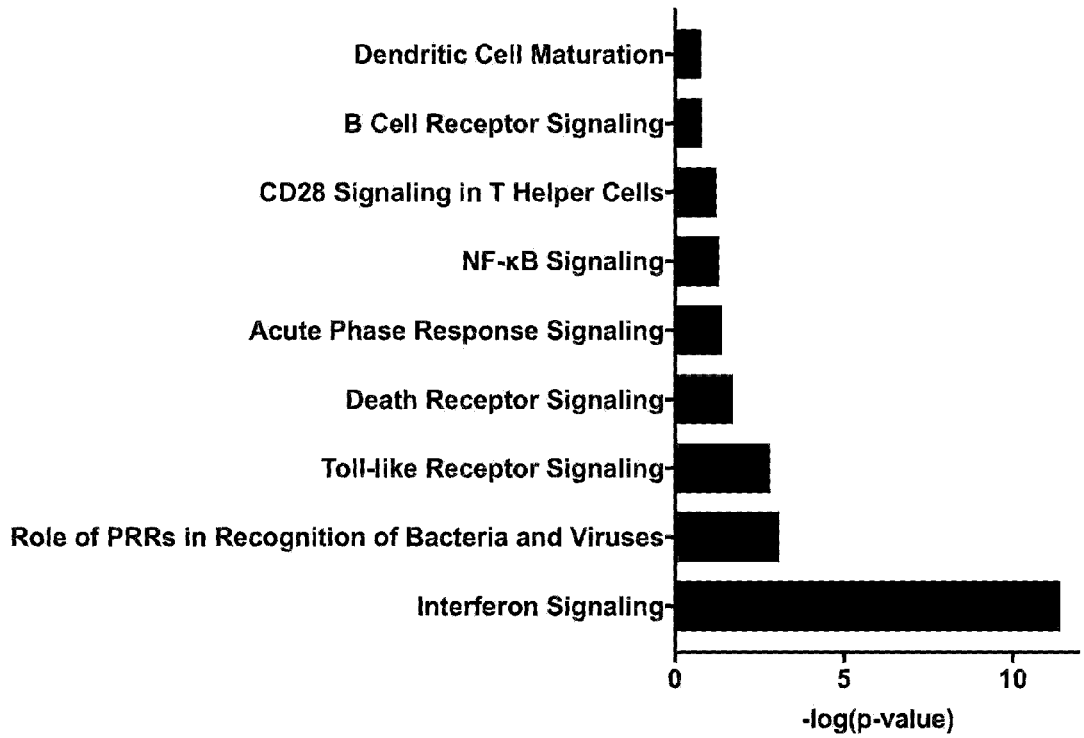
Figure 12E:
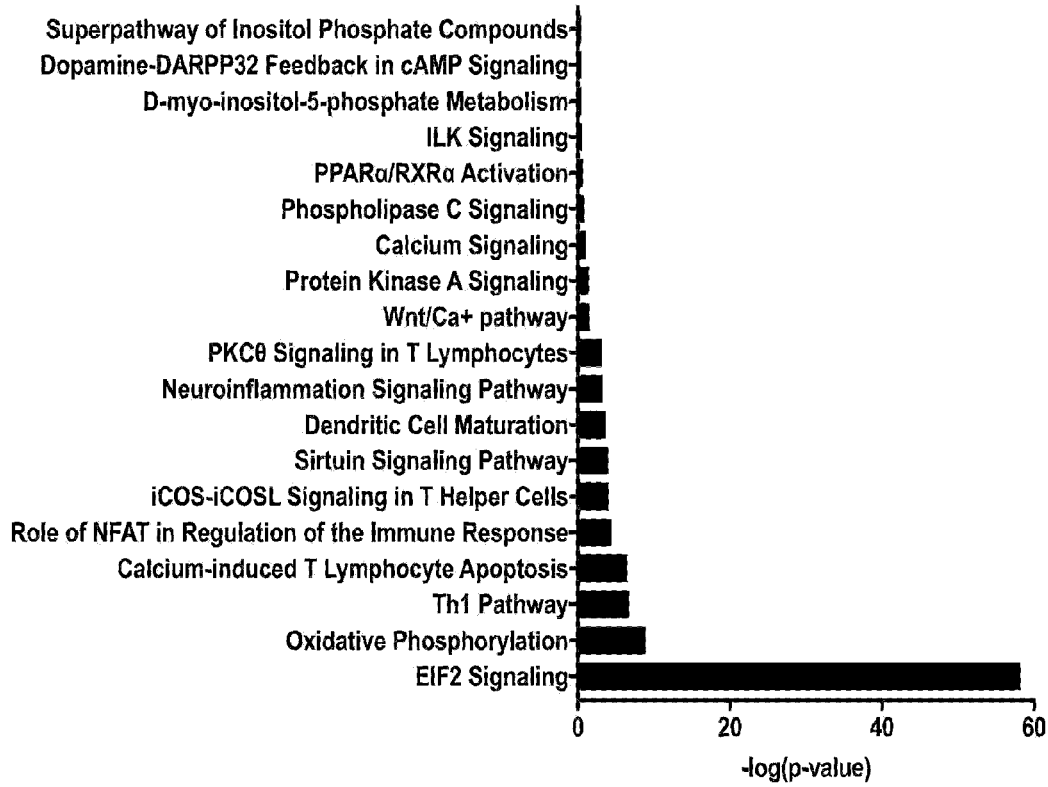
Figure 13A:
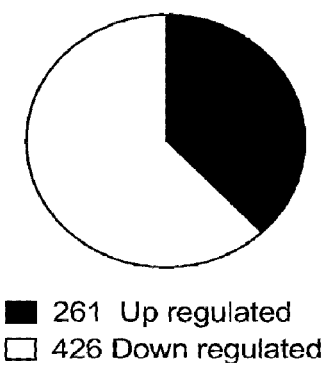
FIG. 13A is a pie chart showing the breakdown of 687 DEG human genes found by alignment of the gene to the human genome (hl 9) by comparing HIV-uninfected CD34-NOG-hIL-34 mice to HIV-infected CD34-NOG-hIL-34 mice. 261 genes were upregulated by HIV infection, and 426 genes were downregulated by HIV infection.
Figure 13B:
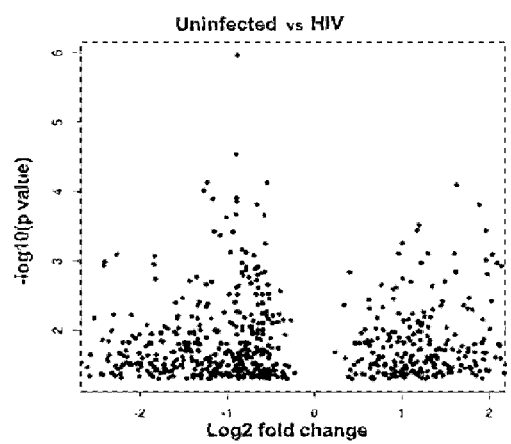
FIG. 13B is a Volcano plot of total DEG (human) created for HIV-uninfected CD34-NOG-hIL-34 mice versus HIV-infected CD34-NOG-hIL-34 mice. X and Y axes show log 2 fold change and log 10 (p value), respectively. Blue dots indicate upregulated genes, green dots indicate downregulated genes, and black dots indicate neutrally regulated genes.

Similarly, in deep sequencing of brain RNA obtained from infected CD34-NOG-hIL-34 mice, HIV-1-related genes such as gag, nef, and env which were not detected in the brain of CD34-NSG mice significantly increased (Colby, D., et al. HIV RNA REBOUND POSTINTERRUPTION IN PERSONS SUPPRESSED IN FIEBIG 1 ACUTE HIV. in Conference on Retroviruses and Opportunistic Infections (IAS-USA, Seattle, Wash., 2017)) (FIG. 9D). All sequenced reads were aligned to the mouse and human reference genomes as described in "[Method]." A total of 82 human myeloid/monocyte/macrophage/microglia-related genes were expressed in human cells of CD34-NOG-hIL-34. The highest expression was MHC class II (CD74) and class I (B2M) (FIG. 12A). Expression of classical macrophage/microglial markers such as AIF1 (IBA1), CD14, CD68, CSF1R, ITGAM (CD11b), P2RY12, CX3CR1, TREM2, and TMEM119 was observed. Various cytokines secreted by microglia such as CCL2, TNF, HGF (IL6), CXC18 (IL8), IL-10, IL1A, and CXC110 were present. PU. 1 (SPI 1), ETV5, and APOE, which are important transcription factors for microglia maintenance and functions, were also recognized (Table 2). Among the human-specific genes (687 genes) that showed different differential expression from the comparison between the HIV-infected CD34-NOG-hIL-34 mice and the uninfected mice, most of the genes (426 genes) showed a significant downregulation in the HIV-infected mice (FIGS. 13A and 13B). Most of the downregulated genes were genes involving EIF2 signaling and oxidative phosphorylation. On the other hand, upregulated genes were genes involving interferon signaling, pattern recognition receptors, toll-like receptor signaling, and death receptor signaling (FIGS. 12B to 12E).

These findings support the fact that human IL-34 plays an important role in human bone marrow derived-monocytes migrating in a postnatal mouse brain and differentiating into microglia.

Tables 2A to 2H: List of genes expressed by microglia

TABLE 2A

| Gene | TPM | Log2 (TPM) |
| --- | --- | --- |
| B2M | 17240.7025 | 14.0735309 |
| MT-CO1 | 11927.96 | 13.5420597 |
| MT-CO2 | 11092.525 | 13.4373002 |
| HLA-DRB1 | 5978.9075 | 12.5456662 |
| APOE | 4766.6875 | 12.2187713 |
| C1QA | 2387.045 | 11.22101 |
| TYROBP | 2290.3425 | 11.1613476 |
| CTSD | 2085.585 | 11.0262364 |
| FCGR3A | 1955.7825 | 10.9335302 |
| STAB1 | 1723.205 | 10.7508786 |
| AIF1 | 1613.7525 | 10.6562036 |
| CD14 | 1081.4125 | 10.0787012 |
| CSF1R | 1034.5725 | 10.014819 |
| CD68 | 963.7575 | 9.91252637 |
| GRN | 930.5725 | 9.86197474 |
| CX3CR1 | 900.0075 | 9.81379321 |
| IGHM | 862.4175 | 9.75224264 |
| CTSH | 755.695 | 9.56166027 |
| TREM2 | 747.2575 | 9.54546166 |
| ITGB2 | 723.2775 | 9.49840546 |
| RGS10 | 706.555 | 9.46465806 |
| SLCO2B1 | 677.38 | 9.40382158 |
| ALOX5AP | 606.6725 | 9.24477411 |
| TNFAIP2 | 536.9825 | 9.06873126 |
| P2RY12 | 526.465 | 9.04019381 |
| S100A9 | 474.6525 | 8.89072787 |
| OLFML3 | 441.1 | 8.78496195 |
| CALR | 435.9675 | 8.76807678 |
| ITGAX | 422.0725 | 8.72134702 |
| ISG15 | 389.355 | 8.60494234 |
| CD37 | 385.3125 | 8.58988518 |
| CYBB | 383.24 | 8.58210434 |
| SPI1 | 348.0175 | 8.44301604 |

TABLE 2A-continued

| Gene | TPM | Log2 (TPM) |
| --- | --- | --- |
| FCGR2A | 291.7375 | 8.18852703 |
| NCF4 | 284.915 | 8.15438777 |
| FUS | 275.245 | 8.10457255 |
| CXCL10 | 272.61 | 8.09069467 |
| GAS6 | 259.35 | 8.01875656 |
| OLR1 | 259.15 | 8.01764358 |
| LAIR1 | 256.285 | 8.00160523 |
| CD163 | 255.3425 | 7.99628987 |

TABLE 2B

| Gene | TPM | Log2 (TPM) |
| --- | --- | --- |
| TSPO | 245.8775 | 7.94179591 |
| GPR34 | 234.75 | 7.87498135 |
| HEXB | 233.1925 | 7.86537758 |
| MX1 | 232.575 | 7.86155222 |
| MERTK | 228.3775 | 7.83527671 |
| TMEM173 | 227.92 | 7.83238372 |
| CASP4 | 212.845 | 7.73365939 |
| CCL2 | 201.3475 | 7.65354375 |
| GAL3ST4 | 195.725 | 7.61268423 |
| IL18 | 194.38 | 7.60273598 |
| BHLHE41 | 193.9175 | 7.59929919 |
| SLC2A5 | 193.68 | 7.59753117 |
| IRF8 | 182.91 | 7.51499014 |
| CPVL | 179.2625 | 7.48592991 |
| HCK | 176.9875 | 7.46750366 |
| ITGAL | 171.3725 | 7.42099181 |
| ANXA11 | 168.15 | 7.39360497 |
| P2RY13 | 161.0875 | 7.33170074 |
| ITGAM | 154.3525 | 7.27008504 |
| PILRA | 150.885 | 7.23730558 |
| TMEM119 | 148.245 | 7.21183964 |
| BLNK | 142.8825 | 7.15868542 |
| TNFRSF1B | 135.825 | 7.08560524 |
| HAVCR2 | 134.61 | 7.07264178 |
| PTAFR | 134.5925 | 7.07245421 |
| FPR1 | 133.11 | 7.05647515 |
| ATP6V0A1 | 132.21 | 7.04668749 |
| GBP2 | 131.925 | 7.04357417 |
| TGFBR1 | 131.4275 | 7.03812337 |
| ACP5 | 131.0275 | 7.03372583 |
| SLC11A1 | 129.4425 | 7.01616757 |
| SOD1 | 128.7525 | 7.00845664 |
| EBI3 | 128.75 | 7.00842862 |
| PTGS1 | 127.04 | 6.98913901 |
| PTOV1 | 125.205 | 6.96814837 |
| TLR2 | 117.9125 | 6.88157286 |
| PTPRC | 116.335 | 6.86214139 |
| PFKFB3 | 112.3975 | 6.81246614 |
| MMP14 | 111.02 | 6.79467579 |
| CCND1 | 108.9075 | 6.7669595 |
| DOK3 | 106.0925 | 6.72917886 |

TABLE 2C

| Gene | TPM | Log2 (TPM) |
| --- | --- | --- |
| NFKB1A | 99.81 | 6.64111246 |
| IL10RA | 98.44 | 6.62117275 |
| RAB31L1 | 98.055 | 6.61551929 |
| SSBP1 | 97.6925 | 6.6101759 |
| ITGB5 | 96.5875 | 6.59376459 |
| SLA | 94.455 | 6.56155526 |
| CD86 | 85.8425 | 6.42362019 |
| PFDN1 | 84.91 | 6.40786257 |
| IL1B | 84.065 | 6.39343336 |
| PTGES2 | 82.8225 | 6.37195085 |
| BCL2L1 | 80.74 | 6.33521168 |
| ENTPD1 | 80.0475 | 6.32278444 |
| CD40 | 79.7175 | 6.31682456 |
| CD33 | 77.4675 | 6.27551928 |

TABLE 2C-continued

| Gene | TPM | Log2 (TPM) |
|---|---|---|
| MX2 | 77.445 | 6.27510019 |
| IF1T1 | 76.23 | 6.25228697 |
| TIMP1 | 76.0125 | 6.24816478 |
| P1K3AP1 | 75.8725 | 6.24550517 |
| CFB | 75.225 | 6.2331403 |
| GBP3 | 75.205 | 6.23275668 |
| ETV5 | 74.4575 | 6.21834527 |
| VCP | 73.4475 | 6.19864148 |
| GBP5 | 72.7575 | 6.18502407 |
| VPS13C | 68.7675 | 6.10365499 |
| PPARD | 65.8475 | 6.04105676 |
| ACSL1 | 65.5675 | 6.03490898 |
| IF1T3 | 63.87 | 5.99706655 |
| IGFBP4 | 60.8375 | 5.92688896 |
| PLAUR | 60.29 | 5.91384682 |
| PPFIBP2 | 59.7 | 5.89965903 |
| CEBPB | 59.1525 | 5.88636724 |
| PABPN1 | 57.535 | 5.84636795 |
| PTPN7 | 57.0725 | 5.83472386 |
| SLAMF7 | 55.8325 | 5.80303325 |
| DKC1 | 55.4 | 5.79181407 |
| PLAU | 54.55 | 5.76950729 |
| AGTRAP | 54.4375 | 5.76652891 |
| TLR1 | 53.77 | 5.74872957 |
| ABCC5 | 52.8425 | 5.72362682 |
| MSRA | 52.185 | 5.70556327 |
| GPR84 | 50.4775 | 5.65756855 |

TABLE 2D

| Gene | TPM | Log2 (TPM) |
|---|---|---|
| TARDBP | 49.1525 | 5.61919289 |
| POLA2 | 49.1175 | 5.61816523 |
| CAMK1 | 48.56 | 5.60169652 |
| AGPAT1 | 48.325 | 5.59469783 |
| SPN | 47.8275 | 5.57976848 |
| RCBTB2 | 47.1175 | 5.55819109 |
| SLC7A8 | 46.82 | 5.54905303 |
| RILPL2 | 46.1825 | 5.52927437 |
| ENPP2 | 45.835 | 5.51837777 |
| PIM1 | 45.4575 | 5.50644644 |
| APBB3 | 45.0175 | 5.49241404 |
| EML1 | 44.26 | 5.46793167 |
| NLRP3 | 43.3325 | 5.43737757 |
| IVNS1ABP | 41.5575 | 5.37703696 |
| CCR5 | 41.1875 | 5.36413466 |
| FZR1 | 39.9925 | 5.32165756 |
| MTSS1 | 39.745 | 5.31270147 |
| RUNX3 | 39.235 | 5.2940693 |
| PSTPIP2 | 38.9475 | 5.28345882 |
| RASGRP3 | 38.945 | 5.28336621 |
| RSAD2 | 36.235 | 5.17939109 |
| SLC31A2 | 35.5 | 5.14974712 |
| SESN1 | 35.4625 | 5.14822234 |
| PROCR | 35.3175 | 5.14231132 |
| ANG | 35.2025 | 5.13760598 |
| ARHGEF7 | 35.2025 | 5.13760598 |
| IFIT2 | 34.7825 | 5.12028973 |
| CCL8 | 33.2775 | 5.05647515 |
| NPEPPS | 32.49 | 5.02192384 |
| MMP9 | 32.125 | 5.00562455 |
| ABCA7 | 31.3925 | 4.97234802 |
| LAG3 | 31.29 | 4.96762975 |
| APP | 31.0925 | 4.95849472 |
| UBE2E2 | 30.8825 | 4.94871764 |
| SLC37A2 | 30.54 | 4.93262816 |
| IL10 | 28.63 | 4.83945577 |
| DNAJC9 | 28.5775 | 4.83680781 |
| MCM3 | 28.325 | 4.82400405 |
| HK3 | 28.2775 | 4.82158267 |
| RUNX1 | 27.4 | 4.77610399 |
| ARHGAP18 | 27.065 | 4.75835648 |

TABLE 2E

| Gene | TPM | Log2 (TPM) |
|---|---|---|
| BATF | 27.0175 | 4.75582228 |
| CRYBB1 | 26.7625 | 4.74214099 |
| RAPGEF2 | 25.5175 | 4.67341509 |
| IGF1 | 25.4775 | 4.67115181 |
| UPP1 | 25.0775 | 4.64832163 |
| F13A1 | 24.7325 | 4.62833617 |
| JAK2 | 24.6875 | 4.62570884 |
| ZDHHC14 | 24.3075 | 4.60332962 |
| GPD2 | 24.2825 | 4.60184506 |
| GADD45B | 23.7875 | 4.57213175 |
| AGER | 23.7425 | 4.56939995 |
| ADRB2 | 22.8375 | 4.51333282 |
| CD69 | 22.815 | 4.51191075 |
| TNF | 22.81 | 4.51159454 |
| GCH1 | 22.705 | 4.50493813 |
| MCM4 | 22.3825 | 4.48429928 |
| CCRL2 | 22.1975 | 4.4723253 |
| SUOX | 21.75 | 4.44429435 |
| PDGFC | 21.71 | 4.44028782 |
| CCL20 | 21.035 | 4.39471991 |
| CD274 | 20.58 | 4.36317108 |
| SPINT1 | 20.3675 | 4.348197 |
| CREM | 20.2 | 4.33628339 |
| CD180 | 19.4075 | 4.27854238 |
| PROS1 | 18.995 | 4.24754781 |
| TRAF1 | 18.885 | 4.23916888 |
| GYS1 | 17.935 | 4.16470584 |
| PMEPA1 | 17.57 | 4.13504229 |
| AKAP10 | 17.45 | 4.12515513 |
| SMAD7 | 17.3775 | 4.11914864 |
| SNAPC2 | 17.1475 | 4.09992635 |
| F11R | 17.045 | 4.09127669 |
| NAMPT | 16.79 | 4.06953033 |
| IL1RN | 16.7425 | 4.06544306 |
| PRIM1 | 16.6475 | 4.05723364 |
| NFKB1Z | 15.5275 | 3.95675366 |
| PHYH | 15.455 | 3.95000175 |
| LRRK2 | 15.4125 | 3.94602899 |
| MCM6 | 14.7175 | 3.87946072 |
| FAM102B | 14.24 | 3.83187724 |
| CABLES1 | 13.75 | 3.78135971 |

TABLE 2G

| Gene | TPM | Log2 (TPM) |
|---|---|---|
| PDE4B | 13.515 | 3.75648961 |
| ARAP2 | 13.425 | 3.74685018 |
| RBL1 | 13.075 | 3.70873904 |
| CASP9 | 13 | 3.70043972 |
| IL1A | 12.9025 | 3.68957873 |
| SLC6A12 | 12.57 | 3.65191274 |
| BIRC3 | 12.54 | 3.64846544 |
| EPAS1 | 12.215 | 3.61058196 |
| IRAK3 | 11.9725 | 3.58165253 |
| GK | 11.94 | 3.57773093 |
| RGS2 | 11.855 | 3.56742376 |
| CABLES2 | 11.5975 | 3.53574194 |
| CSF1 | 11.1675 | 3.48123435 |
| CYSLTR1 | 10.9875 | 3.45779126 |
| RAB11FIP1 | 10.675 | 3.41616416 |
| MALT1 | 10.6125 | 3.40769265 |
| FGD4 | 10.28 | 3.36176836 |
| SDC2 | 10.15 | 3.34340782 |
| NFRKB | 9.51 | 3.24944534 |
| DUSP16 | 9.3425 | 3.22380866 |
| FN1 | 9.28 | 3.21412481 |
| FCGR2B | 9.12 | 3.18903382 |
| GCNT1 | 8.1525 | 3.02724254 |
| FLNB | 7.89 | 2.9800253 |
| SLC36A1 | 7.7825 | 2.96023367 |
| TMEM154 | 7.285 | 2.86492897 |
| CD80 | 6.7825 | 2.76181714 |
| LAMP3 | 6.5525 | 2.71204545 |
| TGM2 | 5.7175 | 2.51538446 |

TABLE 2G-continued

| Gene | TPM | Log2 (TPM) |
|---|---|---|
| HELLS | 5.54 | 2.46988598 |
| TET2 | 4.82 | 2.26903315 |
| CD300E | 4.64 | 2.21412481 |
| CXCL8/IL8 | 4.4525 | 2.15461561 |
| ENC1 | 4.3725 | 2.12845838 |
| ZBED4 | 4.09 | 2.03210084 |
| RMI1 | 3.7975 | 1.92504996 |
| BNIP3 | 3.4675 | 1.79389588 |
| MSH2 | 3.3725 | 1.75381844 |
| CCR2 | 3.285 | 1.71589337 |
| WDHD1 | 2.8275 | 1.49952702 |
| POLA1 | 2.8025 | 1.48671437 |

TABLE 2H

| Gene | TPM | Log2 (TPM) |
|---|---|---|
| ZC3H12C | 2.62 | 1.38956681 |
| XYLT1 | 2.5 | 1.32192809 |
| IFT57 | 2.3225 | 1.2156786 |

TABLE 2H-continued

| Gene | TPM | Log2 (TPM) |
|---|---|---|
| SOCS3 | 2.1875 | 1.12928302 |
| GOLM1 | 2.0575 | 1.04089243 |
| IRF4 | 1.765 | 0.81966818 |
| EXT1 | 1.675 | 0.7441611 |
| DCBLD2 | 1.55 | 0.63226822 |
| DKK1 | 1.4425 | 0.52857132 |
| HGF | 1.415 | 0.50080205 |
| HGF/IL6 | 1.415 | 0.50080205 |
| OPHN1 | 0.87 | −0.2009127 |
| ABCD2 | 0.5925 | −0.7551129 |
| SLC7A11 | 0.4425 | −1.1762506 |
| DGKH | 0.4375 | −1.1926451 |

INDUSTRIAL APPLICABILITY

According to the present invention, a non-human animal that can retain a large number of human microglia, and a method for producing the same are provided. A method for using the non-human animal is also provided.

[Sequence Listing]

The invention claimed is:

1. A non-human mammal expressing human interleukin-34 (1-34) in the brain thereof, wherein a human CD34-positive hematopoietic stem cell is transplanted into the non-human mammal.

2. The non-human mammal according to claim 1, wherein the hematopoietic stem cell differentiates into human microglia in the brain.

3. The non-human mammal according to claim 2, wherein the human microglia express at least one gene selected from the group consisting of CD74, b2m, AIF1, CD14, CD68, CSF1R, ITGAM (CD11b), P2RY12, CX3CR1, TREM2, TMEM119, CCL2, TNF, HGH (IL-6), CXCL8, IL-10, IL-1a, CXCL10, PU.1 (SPI1), ETV5, and APOE.

4. The non-human mammal according to claim 2, wherein the human microglia secrete at least one cytokine selected from the group consisting of CCL2, TNF, HGH (IL-6), CXCL8, IL-10, IL-1a, and CXCL10.

5. The non-human mammal according to claim 1 which is infected with the human immunodeficiency virus (HIV).

6. A method for producing human microglia, comprising obtaining human microglia from the non-human mammal according to claim 2.

* * * * *

```
SEQUENCE LISTING

<160> NUMBER OF SEQ ID NOS: 5

<210> SEQ ID NO 1
<211> LENGTH: 1796
<212> TYPE: DNA
<213> ORGANISM: Homo sapiens
<220> FEATURE:
<221> NAME/KEY: CDS
<222> LOCATION: (556)..(1284)

<400> SEQUENCE: 1
catcagacgg gaagcctgga ctgtgggttg ggggcagcct cagcctctcc aacctggcac      60
ccactgcccg tggcccttag gcacctgctt ggggtcctgg agcccttaa ggccaccagc     120 aaatcctagg agaccgagtc ttggcacgtg aacagagcca gatttcacac tgagcagctg    180
cagtcggaga aatcagagaa agcgtcaccc agccccagat tccgagggc ctgccaggga    240 ctctctcctc ctgctccttg gaaaggaaga ccccgaaaga ccccaagcc accggctcag    300 acctgcttct gggctgccat gggacttgcg gccaccgccc ccggctgtc ctccacgctg    360 ccgggcagat aagggcagct gctgcccttg gggcacctgc tcactcccgc agcccagcca    420
ctcctccagg gccagcccctt ccctgactga gtgaccacct ctgctgcccc gaggccatgt    480
aggccgtgct taggcctctg tggacacact gctgggacg gcgcctgagc tctcagggg     540 acgaggaaca ccacc atg ccc cgg ggc ttc acc tgg ctg cgc tat ctt ggg     591
              Met Pro Arg Gly Phe Thr Trp Leu Arg Tyr Leu Gly
                1               5                   10 atc ttc ctt ggc gtg gcc ttg ggg aat gag cct ttg gag atg tgg ccc      639
Ile Phe Leu Gly Val Ala Leu Gly Asn Glu Pro Leu Glu Met Trp Pro
        15                  20                  25 ttg acg cag aat gag gag tgc act gtc acg ggt ttt ctg cgg gac aag      687
Leu Thr Gln Asn Glu Glu Cys Thr Val Thr Gly Phe Leu Arg Asp Lys
    30                  35                  40 ctg cag tac agg agc cga ctt cag tac atg aaa cac tac ttc ccc atc      735
Leu Gln Tyr Arg Ser Arg Leu Gln Tyr Met Lys His Tyr Phe Pro Ile
45                  50                  55                  60 aac tac aag atc agt gtg cct tac gag ggg gtg ttc aga atc gcc aac      783
Asn Tyr Lys Ile Ser Val Pro Tyr Glu Gly Val Phe Arg Ile Ala Asn
                65                  70                  75
```

```
gtc acc agg ctg cag agg gcc cag gtg agc gag cgg gag ctg cgg tat    831
Val Thr Arg Leu Gln Arg Ala Gln Val Ser Glu Arg Glu Leu Arg Tyr
        80                  85                  90 ctg tgg gtc ttg gtg agc ctc agt gcc act gag tcg gtg cag gac gtg    879
Leu Trp Val Leu Val Ser Leu Ser Ala Thr Glu Ser Val Gln Asp Val
    95                 100                 105 ctg ctc gag ggc cac cca tcc tgg aag tac ctg cag gag gtg gag acg    927
Leu Leu Glu Gly His Pro Ser Trp Lys Tyr Leu Gln Glu Val Glu Thr
110                 115                 120 ctg ctg ctg aat gtc cag cag ggc ctc acg gat gtg gag gtc agc ccc    975
Leu Leu Leu Asn Val Gln Gln Gly Leu Thr Asp Val Glu Val Ser Pro
125                 130                 135                 140 aag gtg gaa tcc gtg ttg tcc ctc ttg aat gcc cca ggg cca aac ctg   1023
Lys Val Glu Ser Val Leu Ser Leu Leu Asn Ala Pro Gly Pro Asn Leu
                145                 150                 155 aag ctg gtg cgg ccc aaa gcc ctg ctg gac aac tgc ttc cgg gtc atg   1071
Lys Leu Val Arg Pro Lys Ala Leu Leu Asp Asn Cys Phe Arg Val Met
            160                 165                 170 gag ctg ctg tac tgc tcc tgc tgt aaa caa agc tcc gtc cta aac tgg   1119
Glu Leu Leu Tyr Cys Ser Cys Cys Lys Gln Ser Ser Val Leu Asn Trp
        175                 180                 185 cag gac tgt gag gtg cca agt cct cag tct tgc agc cca gag ccc tca   1167
Gln Asp Cys Glu Val Pro Ser Pro Gln Ser Cys Ser Pro Glu Pro Ser
    190                 195                 200 ttg cag tat gcg gcc acc cag ctg tac cct ccg ccc ccg tgg tcc ccc   1215
Leu Gln Tyr Ala Ala Thr Gln Leu Tyr Pro Pro Pro Pro Trp Ser Pro
205                 210                 215                 220 agc tcc ccg cct cac tcc acg ggc tcg gtg agg ccg gtc agg gca cag   1263
Ser Ser Pro Pro His Ser Thr Gly Ser Val Arg Pro Val Arg Ala Gln
                225                 230                 235 ggc gag ggc ctc ttg ccc tga gcaccctgga tggtgactgc ggataggggc      1314
Gly Glu Gly Leu Leu Pro
            240 agccagacca gctcccacag gagttcaact gggtctgaga cttcaagggg tggtggtggg  1374 agccccctt gggagaggac ccctgggaag ggtgttttc ctttgagggg gattctgtgc    1434 cacagcaggg ctcagcttcc tgccttccat agctgtcatg gcctcacctg gagcggaggg  1494 gacctgggga cctgaaggtg gatggggaca cagctcctgg cttctcctgg tgctgccctc  1554 actgtccccc cgcctaaagg gggtactgag cctcctgtgg cccgcagcag tgagggcaca  1614 gctgtgggtt gcaggggaga cagccagcac ggcgtggcca ttctatgacc cccagcctg   1674 gcagactggg gagctggggg cagagggcgg tgccaagtgc acatcttgc catagtggat   1734 gctcttccag tttcttttt ctattaaaca ccccacttcc tttggaaaaa aaaaaaaaaa   1794 aa                                                                 1796

<210> SEQ ID NO 2
<211> LENGTH: 242
<212> TYPE: PRT
<213> ORGANISM: Homo sapiens

<400> SEQUENCE: 2

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45
```

```
Ser Arg Leu Gln Tyr Met Lys His Tyr Phe Pro Ile Asn Tyr Lys Ile
 50                  55                  60

Ser Val Pro Tyr Glu Gly Val Phe Arg Ile Ala Asn Val Thr Arg Leu
 65                  70                  75                  80

Gln Arg Ala Gln Val Ser Glu Arg Glu Leu Arg Tyr Leu Trp Val Leu
                 85                  90                  95

Val Ser Leu Ser Ala Thr Glu Ser Val Gln Asp Val Leu Leu Glu Gly
                100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
        210                 215                 220

His Ser Thr Gly Ser Val Arg Pro Val Arg Ala Gln Gly Glu Gly Leu
225                 230                 235                 240

Leu Pro

<210> SEQ ID NO 3
<211> LENGTH: 20
<212> TYPE: DNA
<213> ORGANISM: Artificial Sequence
<220> FEATURE:
<223> OTHER INFORMATION: antisense primer for HIV-1

<400> SEQUENCE: 3
atctggcctg gtgcaatagg                                               20

<210> SEQ ID NO 4
<211> LENGTH: 22
<212> TYPE: DNA
<213> ORGANISM: Artificial Sequence
<220> FEATURE:
<223> OTHER INFORMATION: sense primer for HIV-1

<400> SEQUENCE: 4
acatcaagca gccatgcaaa at                                            22

<210> SEQ ID NO 5
<211> LENGTH: 31
<212> TYPE: DNA
<213> ORGANISM: Artificial Sequence
<220> FEATURE:
<223> OTHER INFORMATION: TaqMan probe

<400> SEQUENCE: 5
catcaatgag gaagctgcag aatgggatag a                                  31
```